(12) United States Patent
Myers et al.

(10) Patent No.: US 8,663,687 B2
(45) Date of Patent: *Mar. 4, 2014

(54) FILM COMPOSITIONS FOR DELIVERY OF ACTIVES

(75) Inventors: Garry L. Myers, Kingsport, TN (US); Richard C. Fuisz, Beverly Hills, CA (US)

(73) Assignee: MonoSol Rx, LLC, Warren, NJ (US)

( * ) Notice: Subject to any disclaimer, the term of this patent is extended or adjusted under 35 U.S.C. 154(b) by 353 days.

This patent is subject to a terminal disclaimer.

(21) Appl. No.: 12/779,316

(22) Filed: May 13, 2010

(65) Prior Publication Data

US 2010/0221309 A1 Sep. 2, 2010

Related U.S. Application Data

(63) Continuation-in-part of application No. 11/634,280, filed on Dec. 5, 2006, which is a continuation of application No. 10/074,272, filed on Feb. 14, 2002, now Pat. No. 7,425,292.

(60) Provisional application No. 60/742,776, filed on Dec. 6, 2005, provisional application No. 60/328,868, filed on Oct. 12, 2001.

(51) Int. Cl.
*A61K 9/14* (2006.01)
*A61K 9/00* (2006.01)
*A61F 13/00* (2006.01)

(52) U.S. Cl.
USPC ........... 424/484; 424/486; 424/487; 424/434; 424/400

(58) Field of Classification Search
CPC ..... A61K 9/0014; A61K 47/34; A61K 47/36; A61K 9/1641; A61K 9/1652; A61K 9/006; A61K 9/7007
USPC .......................... 424/484, 486, 487, 434, 400
See application file for complete search history.

(56) References Cited

U.S. PATENT DOCUMENTS

| | | |
|---|---|---|
| 307,537 A | 11/1884 | Foulks |
| 688,446 A | 12/1901 | Stempel |
| 2,980,554 A | 4/1961 | Gentile et al. |
| 3,007,848 A | 11/1961 | Stroop |
| 3,249,109 A | 5/1966 | Maeth et al. |
| 3,444,858 A | 5/1969 | Russell |
| 3,536,809 A | 10/1970 | Applezweig |
| 3,551,556 A | 12/1970 | Kliment et al. |
| 3,598,122 A | 8/1971 | Zaffaroni |
| 3,632,740 A | 1/1972 | Robinson et al. |
| 3,640,741 A | 2/1972 | Etes |
| 3,641,237 A | 2/1972 | Gould et al. |
| 3,731,683 A | 5/1973 | Zaffaroni |
| 3,753,732 A | 8/1973 | Boroshok |
| 3,814,095 A | 6/1974 | Lubens |
| 3,892,905 A | 7/1975 | Albert |
| 3,911,099 A | 10/1975 | DeFoney et al. |
| 3,972,995 A | 8/1976 | Tsuk et al. |
| 3,996,934 A | 12/1976 | Zaffaroni |
| 4,029,757 A | 6/1977 | Mlodozeniec et al. |
| 4,029,758 A | 6/1977 | Mlodozeniec et al. |
| 4,031,200 A | 6/1977 | Reif |
| 4,123,592 A | 10/1978 | Rainer et al. |
| 4,128,445 A | 12/1978 | Sturzenegger et al. |
| 4,136,145 A | 1/1979 | Fuchs et al. |
| 4,136,162 A | 1/1979 | Fuchs et al. |
| 4,139,627 A | 2/1979 | Lane et al. |
| 4,226,848 A | 10/1980 | Nagai et al. |
| 4,251,400 A | 2/1981 | Columbus |
| 4,292,299 A | 9/1981 | Suzuki et al. |
| 4,294,820 A | 10/1981 | Keith et al. |
| 4,302,465 A | 11/1981 | AF Ekenstam et al. |
| 4,307,075 A | 12/1981 | Martin |
| 4,325,855 A | 4/1982 | Dickmann et al. |
| 4,373,036 A | 2/1983 | Chang et al. |
| 4,406,708 A | 9/1983 | Hesselgren |
| 4,432,975 A | 2/1984 | Libby |
| 4,438,258 A | 3/1984 | Graham |
| 4,460,562 A | 7/1984 | Keith et al. |
| 4,466,973 A | 8/1984 | Rennie |
| 4,503,070 A | 3/1985 | Eby, III |
| 4,515,162 A | 5/1985 | Yamamoto et al. |
| 4,517,173 A | 5/1985 | Kizawa et al. |

(Continued)

FOREIGN PATENT DOCUMENTS

| | | |
|---|---|---|
| DE | 2432925 A1 | 1/1976 |
| DE | 2449865 A1 | 4/1976 |

(Continued)

OTHER PUBLICATIONS

Peh and Wong, Polymeric Films as Vehicle for Buccal Delivery: Swelling, Mechanical, and Bioadhesive Properties, J Pharm Pharmaceut Sci (www.ualberta.cat~csps) 2 (2):53-61, 1999.
Bodmeier. Pharmaceutical Research, vol. 6, No. 8, 1989.
International Search Report for International Application No. PCT/US11/36244 dated Aug. 19, 2011.
Lazaridou et al., "Thermophysical proprties of chitosan, chitosan-starch and chitosan-pullulan films near the glass transition," Carbohydrate Polymers 48: 179-190 (2002).
Repka et al., "Bioadhesive Properties of hydroxypropylcellulose topical films produced by hot melt extrusion," Journal of Controlled Release, 70: 341-351 (2001).
Repka et al., "Influence of Vitamin E TPGS on the properties of hydrophilic films produced by hot melt extrusion", International Journal of Pharmaceutics 202: 63-70 (2000).
Boo, Woong Jae, "Characterization of Thin Film Properties of Melamine Based Dendrimer Nanoparticles", Thesis for Texas A&M University, Dec. 2003.

*Primary Examiner* — Abigail Fisher
(74) *Attorney, Agent, or Firm* — Hoffmann & Baron, LLP

(57) ABSTRACT

The invention relates to the film products and methods of their preparation that demonstrate a non-self-aggregating uniform heterogeneity. Desirably, the films disintegrate in water and may be formed by a controlled drying process, or other process that maintains the required uniformity of the film. Desirably, the films contain at least one active agent, which may be administered to a user topically, transmucosally, vaginally, ocularly, aurally, nasally, transdermally or orally.

32 Claims, 6 Drawing Sheets

(56) References Cited

U.S. PATENT DOCUMENTS

| | | | |
|---|---|---|---|
| 4,529,601 | A | 7/1985 | Broberg et al. |
| 4,529,748 | A | 7/1985 | Wienecke |
| 4,562,020 | A | 12/1985 | Hijiya et al. |
| 4,569,837 | A | 2/1986 | Suzuki et al. |
| 4,593,053 | A | 6/1986 | Jevne et al. |
| 4,608,249 | A | 8/1986 | Otsuka et al. |
| 4,615,697 | A | 10/1986 | Robinson |
| 4,623,394 | A | 11/1986 | Nakamura et al. |
| 4,631,837 | A | 12/1986 | Magoon |
| 4,652,060 | A | 3/1987 | Miyake |
| 4,659,714 | A | 4/1987 | Watt-Smith |
| 4,675,009 | A | 6/1987 | Hymes et al. |
| 4,695,465 | A | 9/1987 | Kigasawa et al. |
| 4,704,119 | A | 11/1987 | Shaw et al. |
| 4,713,239 | A | 12/1987 | Babaian et al. |
| 4,713,243 | A | 12/1987 | Schiraldi et al. |
| 4,722,761 | A | 2/1988 | Cartmell et al. |
| 4,740,365 | A | 4/1988 | Yukimatsu et al. |
| 4,748,022 | A | 5/1988 | Busciglio |
| 4,765,983 | A | 8/1988 | Takayanagi et al. |
| 4,772,470 | A | 9/1988 | Inoue et al. |
| 4,777,046 | A | 10/1988 | Iwakura et al. |
| 4,789,667 | A | 12/1988 | Makino et al. |
| 4,849,246 | A | 7/1989 | Schmidt |
| 4,860,754 | A | 8/1989 | Sharik et al. |
| RE33,093 | E | 10/1989 | Schiraldi et al. |
| 4,876,092 | A | 10/1989 | Mizobuchi et al. |
| 4,876,970 | A | 10/1989 | Bolduc |
| 4,888,354 | A | 12/1989 | Chang et al. |
| 4,894,232 | A | 1/1990 | Reül et al. |
| 4,900,552 | A | 2/1990 | Sanvordeker et al. |
| 4,900,554 | A | 2/1990 | Yanagibashi et al. |
| 4,900,556 | A | 2/1990 | Wheatley et al. |
| 4,910,247 | A | 3/1990 | Haldar et al. |
| 4,915,950 | A | 4/1990 | Miranda et al. |
| 4,925,670 | A | 5/1990 | Schmidt |
| 4,927,634 | A | 5/1990 | Sorrentino et al. |
| 4,927,636 | A | 5/1990 | Hijiya et al. |
| 4,937,078 | A | 6/1990 | Mezei et al. |
| 4,940,587 | A | 7/1990 | Jenkins et al. |
| 4,948,580 | A | 8/1990 | Browning |
| 4,958,580 | A | 9/1990 | Asaba et al. |
| 4,978,531 | A | 12/1990 | Yamazaki et al. |
| 4,981,693 | A | 1/1991 | Higashi et al. |
| 4,981,875 | A | 1/1991 | Leusner et al. |
| 5,023,082 | A | 6/1991 | Friedman et al. |
| 5,023,271 | A | 6/1991 | Vigne et al. |
| 5,024,701 | A | 6/1991 | Desmarais |
| 5,028,632 | A | 7/1991 | Fuisz |
| 5,045,445 | A | 9/1991 | Schultz |
| 5,047,244 | A | 9/1991 | Sanvordeker et al. |
| 5,049,322 | A | 9/1991 | Devissaguet et al. |
| 5,064,717 | A | 11/1991 | Suzuki et al. |
| 5,089,307 | A | 2/1992 | Ninomiya et al. |
| 5,100,591 | A | 3/1992 | Leclef et al. |
| 5,118,508 | A | 6/1992 | Kikuchi et al. |
| 5,158,825 | A | 10/1992 | Altwirth |
| 5,166,233 | A | 11/1992 | Kuroya et al. |
| 5,186,938 | A | 2/1993 | Sablotsky et al. |
| 5,229,164 | A | 7/1993 | Pins et al. |
| 5,234,957 | A | 8/1993 | Mantelle |
| 5,271,940 | A | 12/1993 | Cleary et al. |
| 5,272,191 | A | 12/1993 | Ibrahim et al. |
| 5,344,676 | A | 9/1994 | Kim et al. |
| 5,346,701 | A | 9/1994 | Heiber et al. |
| 5,393,528 | A | 2/1995 | Staab |
| 5,411,945 | A | 5/1995 | Ozaki et al. |
| 5,413,792 | A | 5/1995 | Ninomiya et al. |
| 5,433,960 | A | 7/1995 | Meyers |
| 5,455,043 | A | 10/1995 | Fischel-Ghodsian |
| 5,462,749 | A | 10/1995 | Rencher |
| 5,472,704 | A | 12/1995 | Santus et al. |
| 5,518,902 | A | 5/1996 | Ozaki et al. |
| 5,567,431 | A | 10/1996 | Vert et al. |
| 5,573,783 | A | 11/1996 | Desieno et al. |
| 5,605,696 | A | 2/1997 | Eury et al. |
| 5,620,757 | A | 4/1997 | Ninomiya et al. |
| 5,629,003 | A | 5/1997 | Horstmann et al. |
| 5,629,021 | A | 5/1997 | Wright |
| 5,681,873 | A | 10/1997 | Norton et al. |
| 5,700,478 | A | 12/1997 | Biegajski et al. |
| 5,700,479 | A | 12/1997 | Lundgren |
| 5,766,332 | A | 6/1998 | Graves et al. |
| 5,766,620 | A | 6/1998 | Heiber et al. |
| 5,766,839 | A | 6/1998 | Johnson et al. |
| 5,800,832 | A | 9/1998 | Tapolsky et al. |
| 5,806,284 | A | 9/1998 | Gifford |
| 5,891,461 | A | 4/1999 | Jona et al. |
| 5,891,845 | A | 4/1999 | Myers |
| 5,900,247 | A | 5/1999 | Rault et al. |
| 5,948,430 | A | 9/1999 | Zerbe et al. |
| 6,072,100 | A | 6/2000 | Mooney et al. |
| 6,103,266 | A | 8/2000 | Tapolsky et al. |
| 6,153,210 | A | 11/2000 | Roberts et al. |
| 6,177,096 | B1 | 1/2001 | Zerbe et al. |
| 6,228,399 | B1 * | 5/2001 | Parikh et al. .................. 424/489 |
| 6,231,957 | B1 | 5/2001 | Zerbe et al. |
| 6,284,264 | B1 | 9/2001 | Zerbe et al. |
| 6,375,963 | B1 | 4/2002 | Repka et al. |
| 6,503,532 | B1 | 1/2003 | Murty et al. |
| 6,552,024 | B1 * | 4/2003 | Chen et al. .................. 514/252.16 |
| 6,555,139 | B2 * | 4/2003 | Sharma ........................ 424/489 |
| 6,667,060 | B1 | 12/2003 | Vandecruys et al. |
| 6,720,006 | B2 | 4/2004 | Hanke et al. |
| 6,730,319 | B2 | 5/2004 | Maeder et al. |
| 6,800,329 | B2 | 10/2004 | Horstmann et al. |
| 6,824,829 | B2 | 11/2004 | Berry et al. |
| 7,005,142 | B2 | 2/2006 | Leon |
| 7,425,292 | B2 * | 9/2008 | Yang et al. ................. 264/172.19 |
| 7,579,019 | B2 | 8/2009 | Tapolsky et al. |
| 2001/0006677 | A1 | 7/2001 | McGinity et al. |
| 2001/0022964 | A1 | 9/2001 | Leung et al. |
| 2001/0046511 | A1 | 11/2001 | Zerbe et al. |
| 2003/0107149 | A1 | 6/2003 | Yang et al. |
| 2003/0124176 | A1 | 7/2003 | Hsu et al. |
| 2004/0013731 | A1 | 1/2004 | Chen et al. |
| 2004/0096569 | A1 | 5/2004 | Barkalow et al. |
| 2004/0191302 | A1 | 9/2004 | Davidson |
| 2004/0209057 | A1 | 10/2004 | Enlow et al. |
| 2005/0048102 | A1 | 3/2005 | Tapolsky et al. |
| 2005/0089548 | A1 | 4/2005 | Virgalitto et al. |
| 2005/0118217 | A1 | 6/2005 | Barnhart et al. |
| 2005/0163714 | A1 | 7/2005 | Sukhishvili et al. |
| 2005/0192309 | A1 | 9/2005 | Palermo et al. |
| 2006/0210610 | A1 | 9/2006 | Davidson et al. |
| 2007/0087036 | A1 | 4/2007 | Durschlag et al. |
| 2007/0148097 | A1 | 6/2007 | Finn et al. |
| 2008/0044454 | A1 * | 2/2008 | Yang et al. ..................... 424/439 |
| 2008/0242558 | A1 | 10/2008 | Belcher et al. |
| 2009/0104270 | A1 | 4/2009 | Myers et al. |
| 2009/0181069 | A1 * | 7/2009 | Yang et al. ..................... 424/439 |

FOREIGN PATENT DOCUMENTS

| | | |
|---|---|---|
| DE | 3630603 C2 | 3/1988 |
| EP | 0219762 B1 | 12/1990 |
| EP | 0259749 B1 | 8/1991 |
| EP | 0200508 B1 | 10/1991 |
| EP | 0241178 B1 | 1/1992 |
| EP | 0273069 B1 | 10/1992 |
| EP | 0250187 B1 | 9/1993 |
| EP | 0452446 B1 | 12/1993 |
| EP | 0381194 B1 | 8/1994 |
| EP | 0440462 B1 | 12/1994 |
| EP | 0514691 B1 | 3/1996 |
| EP | 0598606 B1 | 6/1999 |
| EP | 0949925 B1 | 10/1999 |
| EP | 1110546 A1 | 6/2001 |
| EP | 1897543 A1 | 3/2008 |
| GB | 2447016 A | 9/2008 |
| JP | 62126950 | 6/1987 |
| JP | 02265444 | 10/1990 |
| JP | 05147140 | 6/1993 |
| JP | 07322812 | 12/1995 |

(56) References Cited

FOREIGN PATENT DOCUMENTS

| | | |
|---|---|---|
| JP | 2001279100 | 10/2001 |
| WO | 9105540 A1 | 5/1991 |
| WO | 9215289 A1 | 9/1992 |
| WO | 9505416 A2 | 2/1995 |
| WO | 9518046 A1 | 7/1995 |
| WO | 96/25150 A1 | 8/1996 |
| WO | 0018365 A2 | 4/2000 |
| WO | 0042992 A2 | 7/2000 |
| WO | 0170194 A1 | 9/2001 |
| WO | 0191721 A2 | 12/2001 |
| WO | 03030882 A1 | 4/2003 |
| WO | 03030883 A1 | 4/2003 |
| WO | 2005/020933 A2 | 3/2005 |
| WO | 2008011194 A2 | 1/2008 |

* cited by examiner

FILM COMPOSITIONS FOR DELIVERY OF ACTIVES

CROSS-REFERENCE TO RELATED APPLICATIONS

This application is a continuation-in-part of U.S. application Ser. No. 11/634,280, filed Dec. 5, 2006, which claims priority to U.S. Provisional Application No. 60/742,776, filed Dec. 6, 2005, which is a continuation-in-part of U.S. application Ser. No. 10/074,272, filed Feb. 14, 2002, which issued on Sep. 16, 2008 as U.S. Pat. No. 7,425,292, which claims priority to U.S. Provisional Application No. 60/328,868, filed Oct. 12, 2001.

FIELD OF THE INVENTION

The invention relates to rapidly dissolving, self-supporting films and methods of their preparation. The films contain one or more active agents that are uniformly and evenly distributed throughout the film such that the final film has uniformity of content of the active agent(s).

BACKGROUND OF THE RELATED TECHNOLOGY

Films may be used as a delivery system to carry active ingredients such as drugs, pharmaceuticals, and the like. However, historically films and the process of making drug delivery systems therefrom have suffered from a number of unfavorable characteristics that have not allowed them to be used in practice.

Films that incorporate a pharmaceutically active ingredient are disclosed in expired U.S. Pat. No. 4,136,145 to Fuchs, et al. ("Fuchs"). These films may be formed into a sheet, dried and then cut into individual doses. The Fuchs disclosure alleges the fabrication of a uniform film, which includes the combination of water soluble polymers, surfactants, flavors, sweeteners, plasticizers and drugs. These allegedly flexible films are disclosed as being useful for oral, topical or external use. Examples of specific uses disclosed by Fuchs include application of the films to mucosal membrane areas of the body, including the mouth, rectal, vaginal, nasal and ear areas.

Examination of films made in accordance with the process disclosed in Fuchs, however, reveals that such films suffer from the aggregation or conglomeration of particles, i.e., self-aggregation, making them inherently non-uniform. This result can be attributed to Fuchs' process parameters, which although not disclosed likely include the use of relatively long drying times, thereby facilitating intermolecular and interparticulate attractive forces causing crystal growth as the solution gets more saturated during drying as well as exogenous macro phenomena such as convection forces, air flow and the like to form such agglomeration.

The formation of agglomerates randomly distributes the film components and any active present as well. When large dosages are involved, a small change in the dimensions of the film would lead to a large difference in the amount of active per film. If such films were to include low dosages of active, it is possible that portions of the film may be substantially devoid of any active. Since sheets of film are usually cut into unit doses, certain doses may therefore be devoid of or contain an insufficient amount of active for the recommended treatment. Failure to achieve a high degree of accuracy with respect to the amount of active ingredient in the cut film can be harmful to the patient. For this reason, dosage forms formed by processes such as Fuchs, would not likely meet the stringent standards of governmental or regulatory agencies, such as the U.S. Federal Drug Administration ("FDA"), relating to the uniformity of active in dosage forms. Currently, as generally required by various world regulatory authorities, dosage forms may not vary more than 10-15% in the amount of active present. When applied to dosage units based on films, this virtually mandates that uniformity in the film be present.

The problems of self-aggregation leading to non-uniformity of a film were addressed in U.S. Pat. No. 4,849,246 to Schmidt ("Schmidt"). Schmidt specifically pointed out that the methods disclosed by Fuchs did not provide a uniform film and recognized that that the creation of a non-uniform film necessarily prevents accurate dosing, which as discussed above is especially important in the pharmaceutical area. Schmidt abandoned the idea that a mono-layer film, such as described by Fuchs, may provide an accurate dosage form and instead attempted to solve this problem by forming a multi-layered film. Moreover, his process is a multi-step process that adds expense and complexity and is not practical for commercial use.

Other U.S. Patents directly addressed the problems of particle self-aggregation and non-uniformity inherent in conventional film forming techniques. In one attempt to overcome non-uniformity, U.S. Pat. No. 5,629,003 to Horstmann et al. and U.S. Pat. No. 5,948,430 to Zerbe et al. incorporated additional ingredients, i.e. gel formers and polyhydric alcohols respectively, to increase the viscosity of the film prior to drying in an effort to reduce aggregation of the components in the film. These methods have the disadvantage of requiring additional components, which translates to additional cost and manufacturing steps. Furthermore, both methods employ the use the conventional time-consuming drying methods such as a high-temperature air-bath using a drying oven, drying tunnel, vacuum drier, or other such drying equipment. The long length of drying time promotes the aggregation of the active and other components, notwithstanding the use of viscosity modifiers. Such processes also run the risk of exposing the active, i.e., a drug, or vitamin, or other components to prolonged exposure to moisture and elevated temperatures, which may render it ineffective or even harmful.

In addition to the concerns associated with degradation of an active during extended exposure to moisture, the conventional drying methods themselves are unable to provide uniform films. The length of heat exposure during conventional processing, often referred to as the "heat history", and the manner in which such heat is applied, have a direct effect on the formation and morphology of the resultant film product. Uniformity is particularly difficult to achieve via conventional drying methods where a relatively thicker film, which is well-suited for the incorporation of a drug active, is desired. Thicker uniform films are more difficult to achieve because the surfaces of the film and the inner portions of the film do not experience the same external conditions simultaneously during drying. Thus, observation of relatively thick films made from such conventional processing shows a non-uniform structure caused by convection and intermolecular forces and requires greater than 10% moisture to remain flexible. The amount of free moisture can often interfere over time with the drug leading to potency issues and therefore inconsistency in the final product.

Conventional drying methods generally include the use of forced hot air using a drying oven, drying tunnel, and the like. The difficulty in achieving a uniform film is directly related to the rheological properties and the process of water evaporation in the film-forming composition. When the surface of an aqueous polymer solution is contacted with a high temperature air current, such as a film-forming composition passing through a hot air oven, the surface water is immediately evaporated forming a polymer film or skin on the surface. This seals the remainder of the aqueous film-forming composition beneath the surface, forming a barrier through which the remaining water must force itself as it is evaporated in order to achieve a dried film. As the temperature outside the film continues to increase, water vapor pressure builds up under the surface of the film, stretching the surface of the film, and ultimately ripping the film surface open allowing the water vapor to escape. As soon as the water vapor has escaped, the polymer film surface reforms, and this process is repeated, until the film is completely dried. The result of the repeated destruction and reformation of the film surface is observed as a "ripple effect" which produces an uneven, and therefore non-uniform film. Frequently, depending on the polymer, a surface will seal so tightly that the remaining water is difficult to remove, leading to very long drying times, higher temperatures, and higher energy costs.

Other factors, such as mixing techniques, also play a role in the manufacture of a pharmaceutical film suitable for commercialization and regulatory approval. Air can be trapped in the composition during the mixing process or later during the film making process, which can leave voids in the film product as the moisture evaporates during the drying stage. The film frequently collapse around the voids resulting in an uneven film surface and therefore, non-uniformity of the final film product. Uniformity is still affected even if the voids in the film caused by air bubbles do not collapse. This situation also provides a non-uniform film in that the spaces, which are not uniformly distributed, are occupying area that would otherwise be occupied by the film composition. None of the above-mentioned patents either addresses or proposes a solution to the problems caused by air that has been introduced to the film.

It is especially useful to incorporate active agents in a small-scale form into the film. Such small-scale form may include particles of active agents, in such forms as nanoparticles, microparticles, micelles, molecular complexes or other minute forms. As used herein, the term "microparticle" refers to a composite of nanoparticles, which are joined together to form a microparticle-sized mass. A small-scale form of the active agent has a high surface area, allowing the active agent to be more readily absorbed into the body of the user. However, such small-scale forms of the active agent may have the tendency to undesirably agglomerate into larger masses, thereby resulting in difficulty in achieving a uniform distribution of the active agent throughout the film.

Therefore, there is a need for methods and compositions for film products, which use a minimal number of materials or components, and which provide a substantially non-self-aggregating uniform heterogeneity throughout the area of the films. Preferably, such film products would be suitable for delivery of agents through a variety of administration routes, including orally, transmucosally, topically, and other routes of administration, thereby providing convenience of use to the consumer during travel.

Desirably, such films are produced through a selection of a polymer or combination of polymers that will provide a desired viscosity. Also, desirably the films are made through a film-forming process, such as reverse roll coating, or casting and a controlled, and a desirably rapid, drying process which serves to maintain the uniform distribution of non-self-aggregated components. Desirably, the production occurs without the necessary addition of gel formers or polyhydric alcohols and the like which appear to be required in the products and for the processes of prior patents, such as the aforementioned Horstmann and Zerbe patents. Desirably, the films will also incorporate compositions and methods of manufacture that substantially reduce or eliminate air in the film, thereby promoting uniformity in the final film product. Most desirably, the films incorporate small-scale forms of an active agent, including nanoparticles or microparticles of the active agent, while avoiding problems associated with agglomeration of such small-scale active forms.

SUMMARY OF THE INVENTION

The present invention provides a film and a method of forming same. The film can be divided into equally sized units having substantially equal amounts of each compositional component present. This advantage is particularly useful because it permits large area films to be initially formed, and subsequently cut into individual units without concern for whether each unit is compositionally equal. For example, the films of the present invention have particular applicability as delivery systems for topical active agents because each film unit will contain the proper amount of the topical active agent. The films of the present invention also have particular applicability as ingestible films, which are dissolved in the mouth of the user, either rapidly or over a controlled period of time. They may also be used for systemic administration of drugs by applying the films to oral or vaginal mucosal surfaces.

In one aspect of the invention, there is provided a self-supporting film dosage composition including at least one polymer, at least one active agent, where the active agent is in the form of a small-scale particle. The small-scale particle may be, for example, a microparticle or a nanoparticle.

In another aspect of the present invention, there may be provided a method of forming a self-supporting film dosage composition, including the steps of providing a polymeric matrix, forming a small-scale form of at least one active agent, dispersing the small-scale form of the active agent throughout the polymeric matrix, and drying the polymeric matrix so as to form a self-supporting film dosage composition including the small-scale form of the active agent. The small-scale form of the active agent may be in the form of a microparticle or a nanoparticle. The small-scale form of the active agent may be formed through emulsion processing, through milling, and/or through a microfluidics pumping apparatus. In some embodiments, the small-scale form of the active may be formed via a high shear apparatus. The small-scale form of the active may be formed in situ, or may be added as a preformed small-scale form. In cases where the small-scale form of the active is formed in situ, the process of forming the film may be used to stabilize the small-scale form of the active and thus prevent agglomeration. The small-scale form of the active agent may be bonded to one or more ligands.

In one aspect of the present invention, there is provided a self-supporting film. The film includes a water soluble polymer composition including polyethylene oxide and a saccharide-based polymer. The film may also include a small scale form of the active agent. In some aspects, the film may be designed for oral administration. In other aspects, the film may be designed for topical administration. As will be described in further detail below, the film is desirably substantially dissolvable when exposed to a wetting agent, such as water, alcohol or aqueous mixture of alcohols. Particularly with a topical film, contacting the film with the wetting agent permits the agent to be dissolved or dispersed out of the film. The agent may then be applied to a particular surface area, such as an area of the skin.

The present invention also provides a substantially dissolvable, self-supporting film that includes (i) a water soluble polymer composition including at least one saccharide-based polymer; and (ii) one of a hair shampoo, a hair conditioner, a sunscreen, a hand soap, an insect repellant, a moisturizing cream, a shaving cream or gel, an antibiotic, and a dish detergent.

Each of the films of the present invention may be divided into smaller individual film units which may be sized and packaged to provide dosage units for consumption.

In another aspect of the invention, there is a provided a method of making a self-supporting film unit. The process includes the steps of combining a polar solvent, an active agent, desirably in a small-scale form, and a water soluble polymer composition comprising polyethylene oxide and at least one saccharide-based polymer to form a material with a uniform distribution of these components. This material is then formed into a film and fed onto the top side of a substrate surface having top and bottom sides. Heat is applied to the bottom side of the substrate surface in order to dry the film. The dried film is then divided into individual film units.

Also, either alternatively, or in addition to the particular method used to dry the film, the polymer may be selected in order to provide a viscosity that maintains the non-self-aggregating uniform heterogeneity. Techniques may also be used to form the film, including reverse roll coating, deposition, and other techniques.

A dispenser is also provided that includes individual film units of the present invention. The film units may be optionally stacked in a dispenser or in a roll.

A further aspect of the present invention provided is a method of delivering an active agent. This method includes providing a dry film, which at least partially solubilizes when wetted, the film comprising (i) a water soluble polymer composition; and (ii) an active agent. The method may also include contacting the film with a wetting agent that dissolves out the active agent; and administering the dissolved agent to the user. In some embodiments, the water soluble polymer composition may include polyethylene oxide and a saccharide-based polymer.

The present invention also provides a system for applying a topical agent. The system includes a topical agent contained in a water soluble polymeric film comprising polyethylene oxide and a saccharide-based polymer. The system also includes a solvent for dissolving the film. The solvent is provided for direct contact with the film to cause the topical agent to be dissolved or dispersed out of the film, whereby the topical agent can be applied to a surface area in need thereof. Optionally, the system may further include an applicator for applying the topical agent to the surface area in need thereof.

Other aspects of the present invention relate to films for delivery of emulsion compositions. For example, the present invention provides a composition including a solid water soluble polymeric matrix; and a plurality of lipophilic droplets dispersed within the matrix, the composition forming a liquid/liquid emulsion when exposed to water.

Also provided is a self-supporting film for delivery of a liquid/liquid emulsion. The film includes a solid water soluble polymeric matrix having dispersed therein a plurality of lipophilic droplets formed from an emulsion composition.

The present invention further provides methods of preparing emulsion compositions.

One method of preparing an emulsion composition includes providing an aqueous-based emulsion; and converting the aqueous-based emulsion into a non-aqueous dry emulsion, wherein the dry emulsion is in the form of a self-supporting film. The method further includes dissolving the film with an aqueous solvent, thereby reforming the aqueous-based emulsion.

Another method of preparing an emulsion composition includes providing a solid water soluble polymeric film having dispersed therein a plurality of lipophilic droplets; and adding water to dissolve the film, thereby forming an emulsion.

Moreover, the invention provides a method of preparing a film for delivery of an active. The method includes preparing a composition including at least one water soluble polymer; a polar solvent; and an emulsion composition that includes the active; and forming a film from the prepared composition. The method further includes drying the film by a process whereby a plurality of lipophilic droplets including the active become dispersed within the film.

Also provided is a method of preparing a water reconstitutable emulsion composition. The method includes preparing a composition including at least one water soluble polymer; a polar solvent; and an emulsion composition. The method also includes drying the composition to form a dry emulsion including lipophilic droplets dispersed within a solid water soluble polymeric matrix.

The present invention further provides a method of delivering an emulsion composition. The method includes providing a solid water soluble polymeric matrix having dispersed therein a plurality of lipophilic droplets. The method further includes exposing the polymeric matrix to a wetting agent to dissolve the polymeric matrix, thereby forming an emulsion; and applying the emulsion to a surface area in need thereof.

Another aspect of the present invention relates to a system for applying an emulsion. The system includes a dry emulsion including lipophilic droplets dispersed within a water soluble polymeric film. The system further includes a solvent for dissolving the film. The solvent is provided for direct contact with the dry emulsion to cause the dry emulsion to be reconstituted, whereby the reconstituted emulsion can be applied to a surface area in need thereof. Optionally, the system may further include an applicator for applying the reconstituted emulsion to the surface area in need thereof.

A further aspect of the present invention relates to compositions useful for delivering a dispersion of a eutectic composition. For example, the invention provides a composition including a solid water soluble polymeric matrix; and a plurality of droplets of a eutectic composition dispersed within the matrix, the composition forming a dispersion of the eutectic composition when exposed to water.

DETAILED DESCRIPTION OF THE INVENTION

Figure 1:
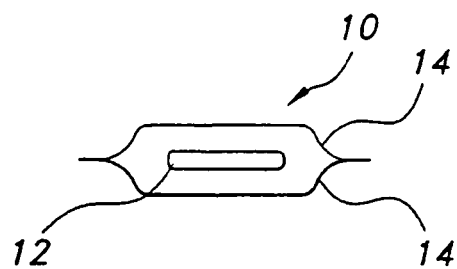
FIG. 1 shows a side view of a package containing a unit dosage film of the present invention.

For the purposes of the present invention the term "non-self-aggregating uniform heterogeneity" refers to the ability of the films of the present invention, which are formed from one or more components in addition to a polar solvent, to provide a substantially reduced occurrence of, i.e. little or no, aggregation or conglomeration of components within the film as is normally experienced when films are formed by conventional drying methods such as a high-temperature air-bath using a drying oven, drying tunnel, vacuum drier, or other such drying equipment. The term heterogeneity, as used in the present invention, includes films that will incorporate a single component, such as a polymer, as well as combinations of components, such as a polymer and an active. Uniform heterogeneity includes the substantial absence of aggregates or conglomerates as is common in conventional mixing and heat drying methods used to form films. It is also to be understood that the terms "agent", "active agent" and "active component" are interchangeable, and refer generally to any substance or composition useful for the prevention or treatment of a condition, including medicaments, bioactive active substances, bioeffective substances, pharmaceutical compositions, therapeutically active compositions, or cosmetic components.

It will be understood that the term "film" includes thin films and sheets, in any shape, including rectangular, square, or other desired shape. The films described herein may be any desired thickness and size suitable for the intended use. For example, a film of the present invention may be sized such that it may be placed into the oral cavity of the user. Other films may be sized for application to the skin of the user, i.e., a topical use. For example, some films may have a relatively thin thickness of from about 0.1 to about 10 mils, while others may have a somewhat thicker thickness of from about 10 to about 30 mils. For some films, especially those intended for topical use, the thickness may be even larger, i.e., greater than about 30 mils. In addition, the term "film" includes single-layer compositions as well as multi-layer compositions, such as laminated films, coatings on films and the like. The composition in its dried film form maintains a uniform distribution of components through the application of controlled drying of the film.

The films of the present invention incorporate one or more agents. An agent may include any substance or composition useful for the prevention or treatment of a condition, including medicaments, bioactive active substances, bioeffective substances, pharmaceutical compositions, therapeutically active compositions, or cosmetic components, which may be administered to a user in any desired means. In some embodiments of the invention, the films are intended for oral administration. In other embodiments, the films are intended for topical administration. As used herein, the term "topical agent" is meant to encompass active agents that are applied to a particular surface area. For example, in one embodiment, a topical agent is applied to an area of the skin. In other embodiments, the topical agent may also be applied to mucosal areas of the body, such as the oral (e.g., buccal, sublingual, tongue), vaginal, ocular, aural, nasal, and anal areas of the body. In other embodiments, a topical agent is applied to a hard surface, such as a particular surface area in need of treatment.

Furthermore, the films of the present invention have a substantially uniform thickness, which is also not provided by the use of conventional drying methods used for drying water-based polymer systems. The absence of a uniform thickness detrimentally affects uniformity of component distribution throughout the area of a given film.

The film products of the present invention are produced by a combination of a properly selected polymer(s), a polar solvent and a topical agent, as well as other fillers known in the art. These films provide a non-self-aggregating uniform heterogeneity of the components within them by utilizing a selected casting or deposition method and a controlled drying process. Examples of controlled drying processes include, but are not limited to, the use of the apparatus disclosed in U.S. Pat. No. 4,631,837 to Magoon ("Magoon"), herein incorporated by reference, as well as controlled drying by rapidly forming a visco-elastic mass in about 10 minutes, and desirably about 4 minutes, such as described in U.S. Pat. Nos. 7,425,292 and 7,357,891, which are herein incorporated by reference in their entireties. Another drying technique for obtaining the films of the present invention is controlled radiation drying, in the absence of uncontrolled air currents, such as infrared and radio frequency radiation (i.e. microwaves).

The objective of the drying process is to provide a method of drying the films that avoids complications, such as the noted "rippling" effect, that are associated with conventional drying methods and which initially dry the upper surface of the film, trapping moisture inside. In conventional oven drying methods, as the moisture trapped inside subsequently evaporates, the top surface is altered by being ripped open and then reformed.

These complications are avoided by the present invention, and a uniform film is provided by drying the bottom surface of the film first or otherwise preventing the formation of polymer film formation (skin) on the top surface of the film prior to drying the depth of the film. This may be achieved by applying heat to the bottom surface of the film with substantially no top air flow, or alternatively by the introduction of controlled microwaves to evaporate the water or other polar solvent within the film, again with substantially no top air flow. In some embodiments, the film is rapidly dried so as to form a visco-elastic structure within the first ten minutes of drying, and more particularly within the first four minutes of drying. Desirably, the film is dried at such a rapid rate that any small-scale forms of an active agent do not undesirably aggregate together. By rapidly drying the wet matrix, a substantial number of the small-scale forms of active agent do not have time to agglomerate.

If desired, the film, which desirably has a substantially uniform distribution of components throughout, is formed by first forming a flowable polymer matrix having a water-soluble polymer composition, at least 30% solvent and an active component. At this point, the flowable polymer matrix should preferably have a uniform distribution of the active component. The flowable polymer matrix may then be cast into a film, as will be described in more detail below. After casting into a film, at least a portion of the solvent may be evaporated from the flowable polymer matrix to form a viscoelastic film. Desirably, the formation of a viscoelastic film is completed within about 10 minutes or fewer, more desirably within about 6 minutes or fewer, and most desirably within about 4 minutes or fewer. This evaporation is useful to maintain the uniform distribution of the active component by locking-in or substantially preventing migration of the active component within the viscoelastic film. Finally, a resulting film from the viscoelastic film may be formed, where the resulting film has a water content of 10% or less and the uniform distribution of active by locking-in or substantially preventing migration of the active component is maintained.

Yet alternatively, drying may be achieved by using balanced fluid flow, such as balanced air flow, where the bottom and top air flows are controlled to provide a uniform film. In such a case, the air flow directed at the top of the film should not create a condition which would cause movement of particles present in the wet film, due to forces generated by the air currents.

Additionally, air currents directed at the bottom of the film should desirably be controlled such that the film does not lift up due to forces from the air. Uncontrolled air currents, either above or below the film, can create non-uniformity in the final film products. The humidity level of the area surrounding the top surface may also be appropriately adjusted to prevent premature closure or skinning of the polymer surface.

This manner of drying the films provides several advantages. Among these are the faster drying times and a more uniform surface of the film, as well as uniform distribution of components for any given area in the film. In addition, the faster drying time allows viscosity to quickly build within the film, further encouraging a uniform distribution of components and decrease in aggregation of components in the final film product. Desirably, the drying of the film will occur within about ten minutes or fewer, or more desirably within about five minutes or fewer.

The present invention yields exceptionally uniform film products when attention is paid to reducing the aggregation of the compositional components. By avoiding the introduction of and eliminating excessive air in the mixing process, selecting polymers and solvents to provide a controllable viscosity and by drying the film in a rapid manner from the bottom up, such films result.

The products and processes of the present invention rely on the interaction among various steps of the production of the films in order to provide films that substantially reduce the self-aggregation of the components within the films. Specifically, these steps include the particular method used to form the film, making the composition mixture to prevent air bubble inclusions, controlling the viscosity of the film forming composition and the method of drying the film. More particularly, a greater viscosity of components in the mixture is particularly useful when the active is not soluble in the selected polar solvent in order to prevent the active from settling out. However, the viscosity must not be too great as to hinder or prevent the chosen method of casting, which desirably includes reverse roll coating due to its ability to provide a film of substantially consistent thickness.

In addition to the viscosity of the film or film-forming components or matrix, there are other considerations taken into account by the present invention for achieving desirable film uniformity. For example, stable suspensions are achieved which prevent solid (such as drug particles) sedimentation in non-colloidal applications. One approach provided by the present invention is to balance the density of the particulate ($\rho_p$) and the liquid phase ($\rho_l$) and increase the viscosity of the liquid phase ($\mu$). For an isolated particle, Stokes law relates the terminal settling velocity (Vo) of a rigid spherical body of radius (r) in a viscous fluid, as follows:

$$V_o = (2gr^2)(\rho_p - \rho_l)/9\mu$$

At high particle concentrations, however, the local particle concentration will affect the local viscosity and density. The viscosity of the suspension is a strong function of solids volume fraction, and particle-particle and particle-liquid interactions will further hinder settling velocity.

Stokian analyses have shown that the incorporation of a third phase, dispersed air or nitrogen, for example, promotes suspension stability. Further, increasing the number of particles leads to a hindered settling effect based on the solids volume fraction. In dilute particle suspensions, the rate of sedimentation, v, can be expressed as:

$$v/V_o = 1/(1 + \kappa\phi)$$

where $\kappa$ = a constant, and $\phi$ is the volume fraction of the dispersed phase. More particles suspended in the liquid phase results in decreased velocity. Particle geometry is also an important factor since the particle dimensions will affect particle-particle flow interactions.

Similarly, the viscosity of the suspension is dependent on the volume fraction of dispersed solids. For dilute suspensions of non-interaction spherical particles, an expression for the suspension viscosity can be expressed as:

$$\mu/\mu_o = 1 + 2.5\phi$$

where $\mu_o$ is the viscosity of the continuous phase and $\phi$ is the solids volume fraction. At higher volume fractions, the viscosity of the dispersion can be expressed as $$\mu/\mu_o = 1 + 2.5\phi + C_1\phi^2 + C_2\phi^3 + \ldots$$

where C is a constant.

The viscosity of the liquid phase is critical and is desirably modified by customizing the liquid composition to a viscoelastic non-Newtonian fluid with low yield stress values. This is the equivalent of producing a high viscosity continuous phase at rest. Formation of a viscoelastic or a highly structured fluid phase provides additional resistive forces to particle sedimentation. Further, flocculation or aggregation can be controlled minimizing particle-particle interactions. The net effect would be the preservation of a homogeneous dispersed phase.

The addition of hydrocolloids to the aqueous phase of the suspension increases viscosity, may produce viscoelasticity and can impart stability depending on the type of hydrocolloid, its concentration and the particle composition, geometry, size, and volume fraction. The particle size distribution of the dispersed phase needs to be controlled by selecting the smallest realistic particle size in the high viscosity medium, i.e., <500 μm. The presence of a slight yield stress or elastic body at low shear rates may also induce permanent stability regardless of the apparent viscosity. The critical particle diameter can be calculated from the yield stress values. In the case of isolated spherical particles, the maximum shear stress developed in settling through a medium of given viscosity can be given as $$\tau_{max}=3V\mu/2r$$

For pseudoplastic fluids, the viscosity in this shear stress regime may well be the zero shear rate viscosity at the Newtonian plateau.

A stable suspension is an important characteristic for the manufacture of a pre-mix composition which is to be fed into the film casting machinery film, as well as the maintenance of this stability in the wet film stage until sufficient drying has occurred to lock-in the particles and matrix into a sufficiently solid form such that uniformity is maintained. For viscoelastic fluid systems, a rheology that yields stable suspensions for extended time period, such as 24 hours, must be balanced with the requirements of high-speed film casting operations. A desirable property for the films is shear thinning or pseudoplasticity, whereby the viscosity decreases with increasing shear rate. Time dependent shear effects such as thixotropy are also advantageous. Structural recovery and shear thinning behavior are important properties, as is the ability for the film to self-level as it is formed.

The rheology requirements for the inventive compositions and films are quite severe. This is due to the need to produce a stable suspension of particles, for example 30-60 wt %, in a viscoelastic fluid matrix with acceptable viscosity values throughout a broad shear rate range. During mixing, pumping, and film casting, shear rates in the range of $10\text{-}10^5$ sec.$^{-1}$ may be experienced and pseudoplasticity is the preferred embodiment.

In film casting or coating, rheology is also a defining factor with respect to the ability to form films with the desired uniformity. Shear viscosity, extensional viscosity, viscoelasticity, structural recovery will influence the quality of the film. As an illustrative example, the leveling of shear-thinning pseudoplastic fluids has been derived as $$\alpha^{(n-1/n)} = \alpha_o^{(n-1/n)} - ((n-1)/(2n-1)) (\tau/K)^{1/n}(2\pi/\lambda)^{(3+n)/n}h^{(2n+1)/n}t$$

where $\alpha$ is the surface wave amplitude, $\alpha_o$ is the initial amplitude, $\lambda$ is the wavelength of the surface roughness, and both "n" and "K" are viscosity power law indices. In this example, leveling behavior is related to viscosity, increasing as n decreases, and decreasing with increasing K.

Desirably, the films or film-forming compositions of the present invention have a very rapid structural recovery, i.e. as the film is formed during processing, it doesn't fall apart or become discontinuous in its structure and compositional uniformity. Such very rapid structural recovery retards particle settling and sedimentation. Moreover, the films or film-forming compositions of the present invention are desirably shear-thinning pseudoplastic fluids. Such fluids with consideration of properties, such as viscosity and elasticity, promote thin film formation and uniformity.

Thus, uniformity in the mixture of components depends upon numerous variables. As described herein, viscosity of the components, the mixing techniques and the rheological properties of the resultant mixed composition and wet casted film are important aspects of the present invention. Additionally, control of particle size and particle shape are further considerations. Desirably, the size of the particulate may be on the order of a microparticle or a nanoparticle, having a particle size of 150 microns or less, for example 100 microns or less. Even smaller sized particles may be used. For example, in especially preferred embodiments, the small scale particle is 1 micron or less in diameter. Moreover, such particles may be spherical, substantially spherical, or non-spherical, such as irregularly shaped particles or ellipsoidally shaped particles. Ellipsoidally shaped particles or ellipsoids are desirable because of their ability to maintain uniformity in the film forming matrix as they tend to settle to a lesser degree as compared to spherical particles. In the case of microparticle-sized actives, the microparticle may include a composite of nanoparticle-sized actives, which join together to form a microparticle-sized active.

In particular, the use of active agents in the form of small scale particles, such as nanoparticles and/or microparticles, is especially preferred due to the high surface area of such small-scale particles. In this form, the active agent has a high entropy structure, which will require less energy to break down and be absorbed in the body of the user. This allows for easier solubility and quicker absorption of the active.

The present invention desirably incorporates methods of forming film compositions in which the small-scale agent particles are maintained in a substantially uniform and non-agglomerated form. Through controlled and rapid drying of films including small-scale forms of particles, such as nanoparticles and microparticles, agglomeration of the particles can be reduced or altogether avoided. This is especially true when a portion of the solvent from a wet film matrix incorporating a dispersion of small-scale forms of the agent is rapidly evaporated to form a visco-elastic mass in a short time, such as less than about 10 minutes, about 6 minutes, or about 4 minutes or less. The visco-elastic mass essentially traps the dispersion of active agent particles in place, reducing or altogether eliminating agglomeration of particles during the rest of the drying process. The resulting film, which is formed from the visco-elastic mass, includes a substantially uniform dispersion of particles, and a lower solvent content, such as about 10% solvent or less, 6% solvent or less, or 4% solvent or less.

A number of techniques may be employed in the mixing stage to prevent bubble inclusions in the final film. To provide a composition mixture with substantially no air bubble formation in the final product, anti-foaming or surface-tension reducing agents are employed. Additionally, the speed of the mixture is desirably controlled to prevent cavitation of the mixture in a manner which pulls air into the mix. Finally, air bubble reduction can further be achieved by allowing the mix to stand for a sufficient time for bubbles to escape prior to drying the film. Desirably, the inventive process first forms a masterbatch of film-forming components without active ingredients or volatile materials. In one embodiment, the active(s) are combined with smaller mixes of the masterbatch just prior to casting. Thus, the masterbatch pre-mix can be allowed to stand for a longer time without concern for instability of the active agent or other ingredients.

When the material is formed including the film-forming polymer and polar solvent in addition to any additives and the active agent, this may be done in a number of steps. For example, the ingredients may all be added together or a pre-mix may be prepared. The advantage of a pre-mix is that all ingredients except for the active may be combined in advance, with the active added just prior to formation of the film. This is especially important for actives that may degrade with prolonged exposure to water, air or another polar solvent.

Figure 6:
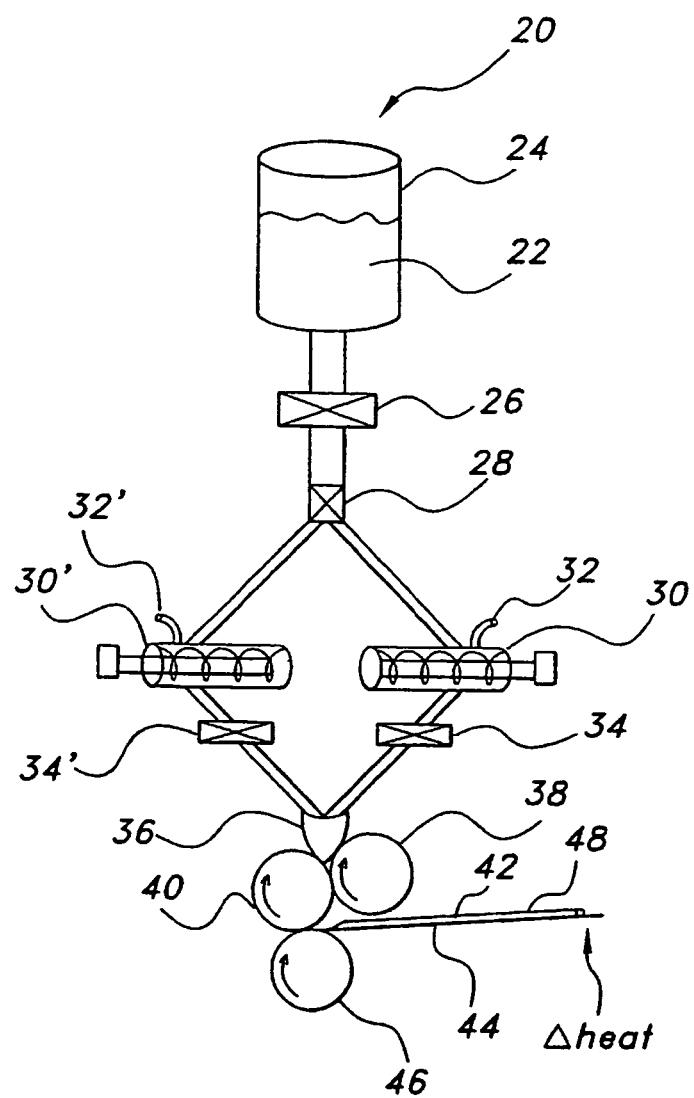
FIG. 6 is a schematic view of an apparatus suitable for preparation of a pre-mix, addition of an active, and subsequent formation of the film.

FIG. 6 shows an apparatus 20 suitable for the preparation of a pre-mix, addition of an active and subsequent formation of a film. The pre-mix or master batch 22, which includes the film-forming polymer, polar solvent, and any other additives except an active agent is added to the master batch feed tank 24. The components for pre-mix or master batch 22 are desirably formed in a mixer (not shown) prior to their addition into the master batch feed tank 24. Then a pre-determined amount of the master batch is controllably fed via a first metering pump 26 and control valve 28 to either or both of the first and second mixers, 30, 30'. The present invention, however, is not limited to the use of two mixers, 30, 30', and any number of mixers may suitably be used. Moreover, the present invention is not limited to any particular sequencing of the mixers 30, 30', such as parallel sequencing as depicted in FIG. 6, and other sequencing or arrangements of mixers, such as series or combination of parallel and series, may suitably be used. The required amount of the active or other ingredient is added to the desired mixer through an opening, 32, 32', in each of the mixers, 30, 30'. Desirably, the residence time of the pre-mix or master batch 22 is minimized in the mixers 30, 30'. While complete dispersion of the active into the pre-mix or master batch 22 is desirable, excessive residence times may result in leaching or dissolving of the active, especially in the case for a soluble drug active. Thus, the mixers 30, 30' are often smaller, i.e. lower residence times, as compared to the primary mixers (not shown) used in forming the pre-mix or master batch 22. After the active has been blended with the master batch pre-mix for a sufficient time to provide a uniform matrix, a specific amount of the uniform matrix is then fed to the pan 36 through the second metering pumps, 34, 34'. The metering roller 38 determines the thickness of the film 42 and applies it to the application roller. The film 42 is finally formed on the substrate 44 and carried away via the support roller 46.

While the proper viscosity uniformity in mixture and stable suspension of particles, and casting method are important in the initial steps of forming the composition and film to promote uniformity, the method of drying the wet film is also important. Although these parameters and properties assist uniformity initially, a controlled rapid drying process ensures that the uniformity will be maintained until the film is dry.

The wet film is then dried using controlled bottom drying or controlled microwave drying, desirably in the absence of external air currents or heat on the top (exposed) surface of the film 48 as described herein. Controlled bottom drying or controlled microwave drying advantageously allows for vapor release from the film without the disadvantages of the prior art. Conventional convection air drying just from the top is not employed because it initiates drying at the top uppermost portion of the film, thereby forming a barrier against fluid flow, such as the evaporative vapors, and thermal flow, such as the thermal energy for drying. Such dried upper portions serve as a barrier to further vapor release as the portions beneath are dried, which results in non-uniform films. As previously mentioned some top air flow can be used to aid the drying of the films of the present invention, but it must not create a condition that would cause particle movement or a rippling effect in the film, both of which would result in non-uniformity. If top air is employed, it is balanced with the bottom air drying to avoid non-uniformity and prevent film lift-up on the carrier belt. A balance top and bottom air flow may be suitable where the bottom air flow functions as the major source of drying and the top air flow is the minor source of drying. The advantage of some top air flow is to move the exiting vapors away from the film thereby aiding in the overall drying process. The use of any top air flow or top drying, however, must be balanced by a number of factors including, but not limited, to rheological properties of the composition and mechanical aspects of the processing. Any top fluid flow, such as air, also must not overcome the inherent viscosity of the film-forming composition. In other words, the top air flow cannot break, distort or otherwise physically disturb the surface of the composition. Moreover, air velocities are desirably below the yield values of the film, i.e., below any force level that can move the liquids in the film-forming compositions. For thin or low viscosity compositions, low air velocity must be used. For thick or high viscosity compositions, higher air velocities may be used. Furthermore, air velocities are desirable low so as to avoid any lifting or other movement of the film formed from the compositions.

Moreover, the films of the present invention may contain particles that are sensitive to temperature, such as volatile ingredients, or drugs, which may have a low degradation temperature. In such cases, the drying temperature may be decreased while increasing the drying time to adequately dry the uniform films of the present invention. Furthermore, bottom drying also tends to result in a lower internal film temperature as compared to top drying. In bottom drying, the evaporating vapors more readily carry heat away from the film as compared to top drying which lowers the internal film temperature. Such lower internal film temperatures often result in decreased drug degradation and decreased loss of certain volatiles, such as flavors.

During film preparation, it may be desirable to dry films at high temperatures. High heat drying produces uniform films, and leads to greater efficiencies in film production. Films containing sensitive active components, however, may face degradation problems at high temperatures. Degradation is the "decomposition of a compound . . . exhibiting well-defined intermediate products." The American Heritage Dictionary of the English Language ($4^{th}$ ed. 2000). Degradation of an active component is typically undesirable as it may cause instability, inactivity, and/or decreased potency of the active component. For instance, if the active component is a drug or bioactive material, this may adversely affect the safety or efficacy of the final pharmaceutical product. Additionally, highly volatile materials will tend to be quickly released from this film upon exposure to conventional drying methods.

Degradation of an active component may occur through a variety of processes, such as, hydrolysis, oxidation, and light degradation, depending upon the particular active component. Moreover, temperature has a significant effect on the rate of such reactions. The rate of degradation typically doubles for every 10° C. increase in temperature. Therefore, it is commonly understood that exposing an active component to high temperatures will initiate and/or accelerate undesirable degradation reactions.

Proteins are one category of useful topical, active agents that may degrade, denature, or otherwise become inactive when they are exposed to high temperatures for extended periods of time. Proteins serve a variety of functions in the body such as enzymes, structural elements, hormones and immunoglobulins. Examples of proteins include enzymes such as pancreatin, trypsin, pancrelipase, chymotrypsin, hyaluronidase, sutilains, streptokinaw, urokinase, altiplase, papain, bromelainsdiastase, structural elements such as collagen, elastin and albumin, hormones such as thyroliberin, gonadoliberin, adrenocorticottropin, corticotrophin, cosyntropin, sometrem, somatropion, prolactin, thyrotropin, somatostatin, vasopressin, felypressin, lypressin, insulin, glucagons, gastrin, pentagastrin, secretin, cholecystokinin-pancreozymin, and immunomodulators which may include polysaccharides in addition to glycoproteins including cytokines which are useful for the inhibition and prevention of malignant cell growth such as tumor growth. A suitable method for the production of some useful glycoproteins is disclosed in U.S. Pat. No. 6,281,337 to Cannon-Carlson, et al., which in incorporated herein in its entirety.

Peptides are another category of useful active agents that have the potential to become inactive when exposed to high temperatures for long periods of time. Peptides may be included in skin care products, for example.

Temperatures that approach 100° C. will generally cause degradation of proteins, certain peptides, as well as nucleic acids. For example, some glycoproteins will degrade if exposed to a temperature of 70° C. for thirty minutes. Proteins from bovine extract are also known to degrade at such low temperatures. DNA also begins to denature at this temperature.

Applicants have discovered, however, that the films of the present invention may be exposed to high temperatures during the drying process without concern for degradation, loss of activity, or excessive evaporation due to the inventive process for film preparation and forming. In particular, the films may be exposed to temperatures that would typically lead to degradation, denaturization, or inactivity of the active component, without causing such problems. According to the present invention, the manner of drying may be controlled to prevent deleterious levels of heat from reaching the active component.

As discussed herein, the flowable mixture is prepared to be uniform in content in accordance with the teachings of the present invention. Uniformity must be maintained as the flowable mass was formed into a film and dried. During the drying process of the present invention, several factors produce uniformity within the film while maintaining the active component at a safe temperature, i.e., below its degradation temperature. First, the films of the present invention have an extremely short heat history, usually only on the order of minutes, so that total temperature exposure is minimized to the extent possible. The films are controllably dried to prevent aggregation and migration of components, as well as preventing heat build up within. Desirably, the films are dried from the bottom. In any drying method, however, it is desirable to rapidly form a visco-elastic mass of the film within the first ten minutes of drying, and even more preferably within the first four minutes of drying. Due to the short heat exposure and evaporative cooling, the film components such as drug or volatile actives remain unaffected by high temperatures, and small-scale particles of active agent are maintained in a non-aggregated fashion. In contrast, skinning on the top surface traps liquid carrier molecules of increased energy within the film, thereby causing the temperature within the film to rise and exposing active components to high, potentially deleterious temperatures.

Second, thermal mixing occurs within the film due to bottom heating and absence of surface skinning Thermal mixing occurs via convection currents in the film. As heat is applied to the bottom of the film, the liquid near the bottom increases in temperature, expands, and becomes less dense. As such, this hotter liquid rises and cooler liquid takes its place. While rising, the hotter liquid mixes with the cooler liquid and shares thermal energy with it, i.e., transfers heat. As the cycle repeats, thermal energy is spread throughout the film.

Robust thermal mixing achieved by the controlled drying process of the present invention produces uniform heat diffusion throughout the film. In the absence of such thermal mixing, "hot spots" may develop. Pockets of heat in the film result in the formation of particle aggregates or danger areas within the film and subsequent non-uniformity. The formation of such aggregates or agglomerations is undesirable because it leads to non-uniform films in which the active may be randomly distributed. Such uneven distribution may lead to large differences in the amount of active per film, which is problematic from a safety and efficacy perspective.

Furthermore, thermal mixing helps to maintain a lower overall temperature inside the film. Although the film surfaces may be exposed to a temperature above that at which the active component degrades, the film interior may not reach this temperature. Due to this temperature differential, the active does not degrade.

For instance, the films of the present invention desirably are dried for 10 minutes or less. Drying the films at 80° C. for 10 minutes produces a temperature differential of about 5° C. This means that after 10 minutes of drying, the temperature of the inside of the film is 5° C. less than the outside exposure temperature. In many cases, however, drying times of less than 10 minutes are sufficient, such as 4 to 6 minutes. Drying for 4 minutes may be accompanied by a temperature differential of about 30° C., and drying for 6 minutes may be accompanied by a differential of about 25° C. Due to such large temperature differentials, the films may be dried at efficient, high temperatures without causing heat sensitive actives to degrade.

Figure 7:
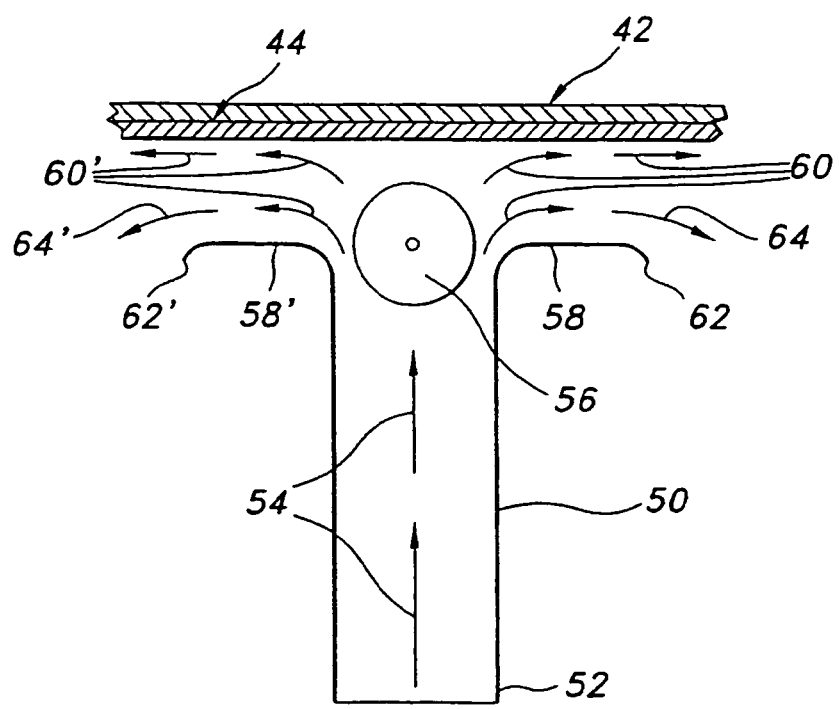
FIG. 7 is a schematic view of an apparatus suitable for drying the films of the present invention.
Figure 8:
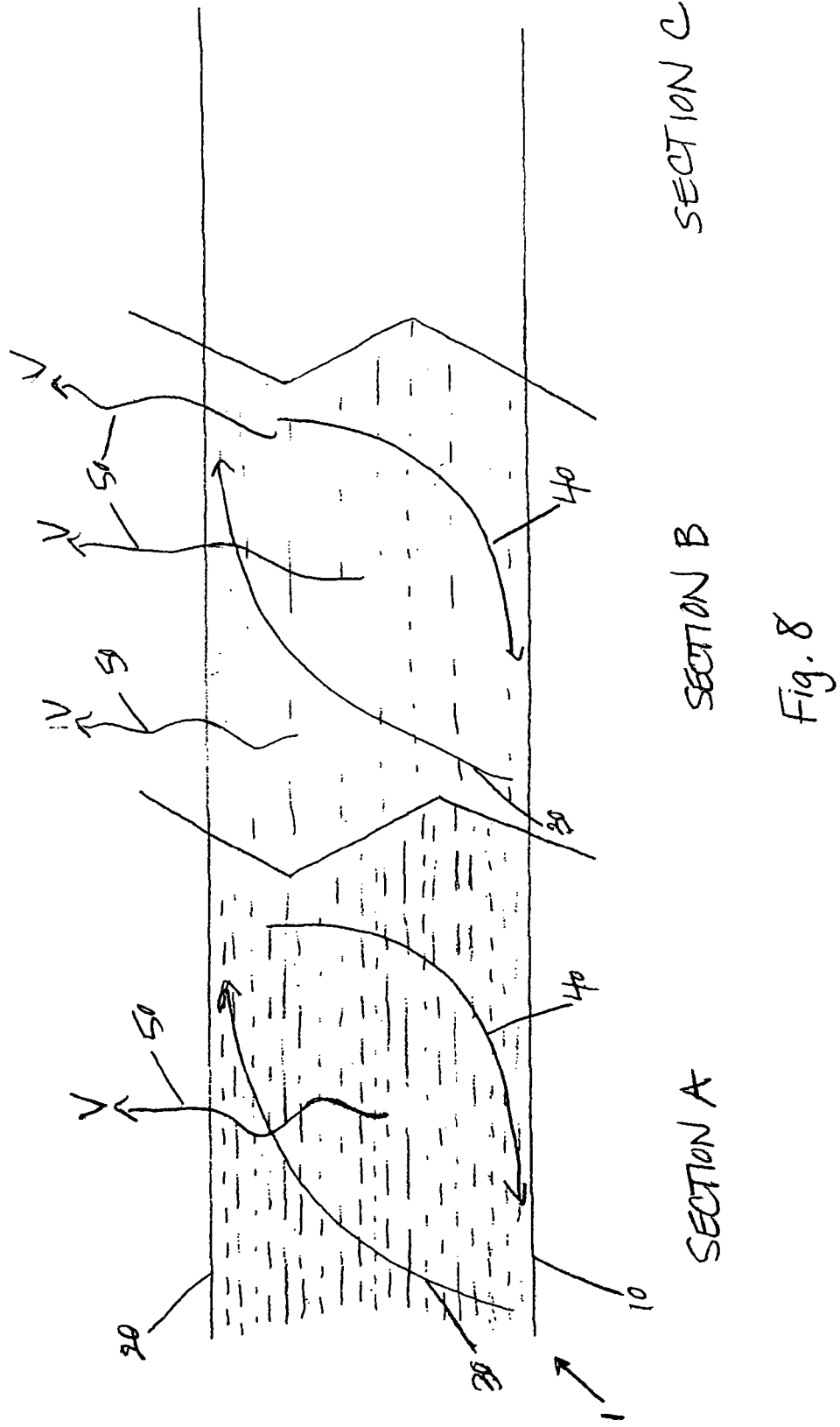
FIG. 8 is a sequential representation of the drying process of the present invention.

FIG. 8 is a sequential representation of the drying process of the present invention. After mechanical mixing, the film may be placed on a conveyor for continued thermal mixing during the drying process. At the outset of the drying process, depicted in Section A, the film 1 preferably is heated from the bottom 10 as it is travels via conveyor (not shown). Heat may be supplied to the film by a heating mechanism, such as, but not limited to, the dryer depicted in FIG. 7. As the film is heated, the liquid carrier, or volatile ("V"), begins to evaporate, as shown by upward arrow 50. Thermal mixing also initiates as hotter liquid, depicted by arrow 30, rises and cooler liquid, depicted by arrow 40, takes its place. Because no skin forms on the top surface 20 of the film 1, as shown in Section B the volatile liquid continues to evaporate 50 and thermal mixing 30/40 continues to distribute thermal energy throughout the film. Once a sufficient amount of the volatile liquid has evaporated, thermal mixing has produced uniform heat diffusion throughout the film 1. The resulting dried film 1 is a visco-elastic solid, as depicted in Section C. The components desirably are locked into a uniform distribution throughout the film. It may be desired to form the visco-elastic solid rapidly, for example within the first 10 minutes or less, desirably within the first 6 minutes or less, and most desirably within the first 4 minutes or less. Although minor amounts of liquid carrier, i.e., water, may remain subsequent to formation of the visco-elastic film, the film may be dried further without affecting the desired heterogeneity of the film, if desired.

Furthermore, particles or particulates may be added to the film-forming composition or material after the composition or material is cast into a film. For example, particles may be added to the film 42 prior to the drying of the film 42. Particles may be controllably metered to the film and disposed onto the film through a suitable technique, such as through the use of a doctor blade (not shown), which is a device which marginally or softly touches the surface of the film and controllably disposes the particles onto the film surface. Other suitable, but non-limiting, techniques include the use of an additional roller to place the particles on the film surface, spraying the particles onto the film surface, and the like. The particles may be placed on either or both of the opposed film surfaces, i.e., the top and/or bottom film surfaces. Desirably, the particles are securably disposed onto the film, such as being embedded into the film. Moreover, such particles are desirably not fully encased or fully embedded into the film, but remain exposed to the surface of the film, such as in the case where the particles are partially embedded or partially encased.

The particles may be any useful topical agents(s). Useful topical agents include personal care products and medicinal agents. In some embodiments, the topical agent may be selected from the following: soaps, body washing agents, hair shampoos, hair conditioners, hair styling agents, moisturizing agents, underarm deodorants and/or antiperspirants, shaving creams or gels, sunscreens and insect repellants. In some further embodiments, the topical agent may be selected from antibacterial agents, acne medications, hormones, agents for preventing motion sickness and anesthetics, such as prilocaine, lidocaine and combinations thereof.

Although the inventive process is not limited to any particular apparatus for the above-described desirable drying, one particular useful drying apparatus 50 is depicted in FIG. 7. Drying apparatus 50 is a nozzle arrangement for directing hot fluid, such as but not limited to hot air, towards the bottom of the film 42 which is disposed on substrate 44. Hot air enters the entrance end 52 of the drying apparatus and travels vertically upward, as depicted by vectors 54, towards air deflector 56. The air deflector 56 redirects the air movement to minimize upward force on the film 42. As depicted in FIG. 7, the air is tangentially directed, as indicated by vectors 60 and 60', as the air passes by air deflector 56 and enters and travels through chamber portions 58 and 58' of the drying apparatus 50. With the hot air flow being substantially tangential to the film 42, lifting of the film as it is being dried is thereby minimized. While the air deflector 56 is depicted as a roller, other devices and geometries for deflecting air or hot fluid may suitable be used. Furthermore, the exit ends 62 and 62' of the drying apparatus 50 are flared downwardly. Such downward flaring provides a downward force or downward velocity vector, as indicated by vectors 64 and 64', which tend to provide a pulling or drag effect of the film 42 to prevent lifting of the film 42. Lifting of the film 42 may not only result in non-uniformity in the film or otherwise, but may also result in non-controlled processing of the film 42 as the film 42 and/or substrate 44 lift away from the processing equipment.

Monitoring and control of the thickness of the film also contributes to the production of a uniform film by providing a film of uniform thickness. The thickness of the film may be monitored with gauges such as Beta Gauges. A gauge may be coupled to another gauge at the end of the drying apparatus, i.e. drying oven or tunnel, to communicate through feedback loops to control and adjust the opening in the coating apparatus, resulting in control of uniform film thickness. Alternatively, the thickness of the film can also be controlled by manual measurement during the production process to achieve the desired thickness of the film.

The film products are generally formed by combining a properly selected polymer and polar solvent, as well as any topical agent or filler as desired. Desirably, the solvent content of the combination is at least about 30% by weight of the total combination. The material formed by this combination is formed into a film, desirably by roll coating, and then dried, desirably by a rapid and controlled drying process to maintain the uniformity of the film, more specifically, a non-self-aggregating uniform heterogeneity. The resulting film will desirably contain less than about 10% by weight solvent, more desirably less than about 8% by weight solvent, even more desirably less than about 6% by weight solvent and most desirably less than about 2%. The solvent may be water, a polar organic solvent including, but not limited to, ethanol, isopropanol, acetone, methylene chloride, or any combination thereof.

Consideration of the above discussed parameters, such as, but not limited to, rheology properties, viscosity, mixing method, casting method and drying method, also impact material selection for the different components of the present invention. Furthermore, such consideration with proper material selection provides the compositions of the present invention, including a pharmaceutical and/or cosmetic dosage form or film product having no more than a 10% variance of a pharmaceutical and/or cosmetic active per unit area. In other words, the uniformity of the present invention is determined by the presence of no more than a 10% by weight of pharmaceutical and/or cosmetic variance throughout the matrix. Desirably, the variance is less than 5% by weight, less than 2% by weight, less than 1% by weight, or less than 0.5% by weight.

Film-Forming Polymers

The film units of the present invention include at least one water soluble polymer. The films may also include water swellable or water insoluble polymers, if desired.

In some embodiments, the self-supporting film includes a saccharide-based polymer, which is water soluble. For example, the saccharide-based polymer may be cellulose or a cellulose derivative. Specific examples of useful saccharide-based, water soluble polymers include, but are not limited to, polydextrose, pullulan, hydroxypropylmethyl cellulose (HPMC), hydroxyethyl cellulose (HPC), hydroxypropyl cellulose, carboxymethyl cellulose, sodium aginate, xanthan gum, tragancanth gum, guar gum, acacia gum, arabic gum, starch, gelatin, and combinations thereof.

In some preferred embodiments, the saccharide-based polymer may be at least one cellulosic polymer, polydextrose, or combinations thereof. The film may also include non-saccharide-based, water soluble or water insoluble polymers. Examples of non-saccharide based, water soluble polymers include polyethylene oxide, polyvinylpyrrolidone, polyvinyl alcohol, polyethylene glycol, polyacrylic acid, methylmethacrylate copolymer, carboxyvinyl copolymers, and combinations thereof. Specific examples of useful water insoluble polymers include, but are not limited to, ethyl cellulose, hydroxypropyl ethyl cellulose, cellulose acetate phthalate, hydroxypropyl methyl cellulose phthalate and combinations thereof.

In some further preferred embodiments, the polymer is a combination of hydroxypropylmethyl cellulose and polyethylene oxide. In some other preferred embodiments, the polymer is a combination of polydextrose and polyethylene oxide. In still further preferred embodiments, the polymer is a combination of polydextrose, hydroxy propylmethyl cellulose and polyethylene oxide.

As used herein, the phrase "water soluble polymer" and variants thereof refer to a polymer that is at least partially soluble in water, and desirably fully or predominantly soluble in water, or absorbs water. In some embodiments, the film unit of the present invention is at least partially dissolvable when exposed to a wetting agent. In some other embodiments, the inventive film unit is substantially dissolvable when exposed to a wetting agent.

Polymers that absorb water are often referred to as being water swellable polymers. The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least 20 percent by weight water uptake. Water swellable polymers having a 25 or greater percent by weight water uptake are also useful. Films or dosage forms of the present invention formed from such water soluble polymers are desirably sufficiently water soluble to be dissolvable upon contact with bodily fluids.

Other polymers useful for incorporation into the films of the present invention include biodegradable polymers, copolymers, block polymers and combinations thereof. Among the known useful polymers or polymer classes which meet the above criteria are: poly(glycolic acid) (PGA), poly (lactic acid) (PLA), polydioxanoes, polyoxalates, poly($\alpha$-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of $\alpha$-amino acids, copolymers of $\alpha$-amino acids and caproic acid, copolymers of $\alpha$-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338°-347° F. (170°-175° C.); lactide/glycolide 100 L, believed to be 100% glycolide having a melting point within the range of 437°-455° F. (225°-235° C.); lactide/glycoli 85/15, believed to be 85% lactide and 15% glycolide with a melting point within the range of 338°-347° F. (170°-175° C.); and lactide/glycolide 50/50, believed to be a copolymer of 50% lactide and 50% glycolide with a melting point within the range of 338°-347° F. (170°-175° C.).

The Biodel materials represent a family of various polyanhydrides which differ chemically.

Although a variety of different polymers may be used, it is desired to select polymers to provide a desired viscosity of the mixture prior to drying. For example, if the topical agent or other components are not soluble in the selected solvent, a polymer that will provide a greater viscosity is desired to assist in maintaining uniformity. On the other hand, if the components are soluble in the solvent, a polymer that provides a lower viscosity may be preferred.

The polymer plays an important role in affecting the viscosity of the film. Viscosity is one property of a liquid that controls the stability of the topical agent in an emulsion, a colloid or a suspension. Generally the viscosity of the matrix will vary from about 400 cps to about 100,000 cps, preferably from about 800 cps to about 60,000 cps, and most preferably from about 1,000 cps to about 40,000 cps. Desirably, the viscosity of the film-forming matrix will rapidly increase upon initiation of the drying process.

The viscosity may be adjusted based on the selected topical agent component, depending on the other components within the matrix. For example, if the component is not soluble within the selected solvent, a proper viscosity may be selected to prevent the component from settling which would adversely affect the uniformity of the resulting film. The viscosity may be adjusted in different ways. To increase viscosity of the film matrix, the polymer may be chosen of a higher molecular weight or crosslinkers may be added, such as salts of calcium, sodium and potassium. The viscosity may also be adjusted by adjusting the temperature or by adding a viscosity increasing component. Components that will increase the viscosity or stabilize the emulsion/suspension include higher molecular weight polymers and polysaccharides and gums, which include without limitation, alginate, carrageenan, hydroxypropyl methyl cellulose, locust bean gum, guar gum, xanthan gum, dextran, gum arabic, gellan gum and combinations thereof.

It has also been observed that certain polymers which when used alone would ordinarily require a plasticizer to achieve a flexible film, can be combined without a plasticizer and yet achieve flexible films. For example, HPMC and HPC when used in combination provide a flexible, strong film with the appropriate plasticity and elasticity for manufacturing and storage. No additional plasticizer or polyalcohol is needed for flexibility.

Additionally, polyethylene oxide (PEO), when used alone or in combination with a hydrophilic cellulosic polymer and/or polydextrose, achieves flexible, strong films. Additional plasticizers or polyalcohols are not needed for flexibility. Non-limiting examples of suitable cellulosic polymers for combination with PEO include HPC and HPMC. PEO and HPC have essentially no gelation temperature, while HPMC has a gelation temperature of 58-64° C. (Methocel EF available from Dow Chemical Co.). Moreover, these films are sufficiently flexible even when substantially free of organic solvents, which may be removed without compromising film properties. As such, if there is no solvent present, then there is no plasticizer in the films. PEO based films also exhibit good resistance to tearing, little or no curling, and fast dissolution rates when the polymer component contains appropriate levels of PEO.

To achieve the desired film properties, the level and/or molecular weight of PEO in the polymer component may be varied. Modifying the PEO content affects properties such as tear resistance, dissolution rate, and adhesion tendencies. Thus, one method for controlling film properties is to modify the PEO content. For instance, in some embodiments rapid dissolving films are desirable. By modifying the content of the polymer component, the desired dissolution characteristics can be achieved.

In accordance with the present invention, PEO desirably ranges from about 20% to 100% by weight in the polymer component. In some embodiments, the amount of PEO desirably ranges from about 1 mg to about 200 mg. The hydrophilic cellulosic polymer and/or polydextrose ranges from about 0% to about 80% by weight, or in a ratio of up to about 4:1 with the PEO, and desirably in a ratio of about 1:1.

In some embodiments, it may be desirable to vary the PEO levels to promote certain film properties. To obtain films with high tear resistance and fast dissolution rates, levels of about 50% or greater of PEO in the polymer component are desirable. To achieve adhesion prevention, i.e., preventing the film from adhering to the roof of the mouth, PEO levels of about 20% to 75% are desirable. In some embodiments, however, adhesion to the roof of the mouth may be desired, such as for administration to animals or children. In such cases, higher levels of PEO may be employed. More specifically, structural integrity and dissolution of the film can be controlled such that the film can adhere to mucosa and be readily removed, or adhere more firmly and be difficult to remove, depending on the intended use.

The molecular weight of the PEO may also be varied. High molecular weight PEO, such as about 4 million, may be desired to increase mucoadhesivity of the film. More desirably, the molecular weight may range from about 100,000 to 900,000, more desirably from about 100,000 to 600,000, and most desirably from about 100,000 to 300,000. In some embodiments, it may be desirable to combine high molecular weight (600,000 to 900,000) with low molecular weight (100,000 to 300,000) PEOs in the polymer component.

For instance, certain film properties, such as fast dissolution rates and high tear resistance, may be attained by combining small amounts of high molecular weight PEOs with larger amounts of lower molecular weight PEOs. Desirably, such compositions contain about 60% or greater levels of the lower molecular weight PEO in the PEO-blend polymer component.

To balance the properties of adhesion prevention, fast dissolution rate, and good tear resistance, desirable film compositions may include about 50% to 75% low molecular weight PEO, optionally combined with a small amount of a higher molecular weight PEO, with the remainder of the polymer component containing a hydrophilic cellulosic polymer (HPC or HPMC) and/or polydextrose.

In some embodiments the film may include polyvinyl alcohol (PVA), alone or in combination with at least one additional polymer Examples of an additional polymer include a cellulosic polymer, starch, polyvinyl pyrrolidone (PVP), polyethylene oxide (PEO), an alginate, a pectin, or combinations thereof. PVA can be used in the films to improve film strength and/or to vary and slow dissolution times. The films are especially useful for the delivery of cosmetics, nutraceuticals and pharmaceuticals. In a preferred embodiment, the film includes PVA without any added plasticizers. For example, the film can include both PVA, which provides strength to the film and PEO, which provides flexibility to the film and nay obviate the need for a plasticizer.

PVA can be used in varying amounts depending upon the product application and characteristics desired. For example, in general, a larger amount of PVA will increase film strength and increase dissolution time. For films that require high active dosing, PVA can be used effectively at minimum amount of 0.5, preferably 1%, more preferably 5%, by weight of the film, to improve film strength. The PVA an be effectively used at a maximum amount, for example, 80%, preferably 50%, more preferably 25% by weight of the film. For slowing dissolution time, PVA can be used at levels as high as 80%. A film containing an active can be coated on one or both surfaces with a PVA containing layer to modify the dissolution of the film and the release of an active from the film.

High loading of actives can decrease the strength and flexibility of the film. Including PVA in the film either alone or in combination with at least one other polymer can increase the tensile strength of the film. Also, drug particles or taste-masked or coated or modified release drug particles may have a larger particle size, which can make loading of these particles into the film difficult. PVA can increase the viscosity of the film solution to allow improved drug loading.

Controlled Release Films

The term "controlled release" is intended to mean the release of the agent at a pre-selected or desired rate. For example, in embodiments where the agent is a medicament, it may be desirable to control its release from the film. This rate will vary depending upon the application. Desirable rates include fast or immediate release profiles as well as delayed, sustained or sequential release. Combinations of release patterns, such as initial spiked release followed by lower levels of sustained release of active are contemplated. Pulsed releases of the agent are also contemplated.

Dissolvable films generally fall into three main classes: fast dissolving, moderate dissolving and slow dissolving. Films of the present invention are dissolvable in the presence of liquid, such as in the oral cavity of the user or when mixed with a liquid, such as water. Fast dissolving films generally dissolve in about 1 second to about 30 seconds. Moderate dissolving films generally dissolve in about 1 to about 30 minutes, and slow dissolving films generally dissolve in more than 30 minutes, e.g., up to about 60 minutes or more. Fast dissolving films may consist of low molecular weight hydrophilic polymers (i.e., polymers having a molecular weight between about 1,000 to 200,000). In contrast, slow dissolving films generally have high molecular weight polymers (i.e., having a molecular weight in the millions).

Moderate dissolving films tend to fall in between the fast and slow dissolving films. Moderate dissolving films dissolve rather quickly, but also have a good level of mucoadhesion. Moderate films are also flexible, quickly wettable, and are typically non-irritating to the user. For oral-dissolving films, moderate dissolving films are preferred, since such films provide a quick enough dissolution rate (between about 1 minute and about 5 minutes), while providing an acceptable mucoadhesion level such that the film is not easily removable once it is placed in the oral cavity of the user.

The polymers that are chosen for the films of the present invention may also be chosen to allow for controlled disintegration of the agent. This may be achieved by providing a substantially water insoluble film that incorporates an agent that will be released from the film over time. This may be accomplished by incorporating a variety of different soluble or insoluble polymers and may also include biodegradable polymers in combination. Alternatively, coated controlled release agent particles may be incorporated into a readily soluble film matrix to achieve the controlled release property of the agent.

The convenience of administering a single dose of a medication which releases ingredients in a controlled fashion over an extended period of time, as opposed to the administration of a number of single doses at regular intervals has long been recognized in the pharmaceutical arts. The advantage to the patient and clinician in having consistent and uniform levels of medication delivered to the body over an extended period of time are likewise recognized.

The agents employed in the present invention may be incorporated into the film compositions of the present invention in a controlled release form. For example, particles of a drug may be coated with polymers, such as ethyl cellulose or polymethacrylate, which are commercially available under brand names such as Aquacoat ECD and Eudragit E-100, respectively. Solutions of a drug may also be absorbed on such polymer materials and incorporated into the inventive film compositions. Other components may also be employed in such controlled release compositions.

When an active agent is introduced to the film, the amount of agent per unit area is determined by the uniform distribution of the film. For example, when the films are cut into individual units, the amount of the agent in the unit can be known with a great deal of accuracy. This is achieved because the amount of the agent in a given area is substantially identical to the amount of agent in an area of the same dimensions in another part of the film. The accuracy in dosage is particularly advantageous when the agent is a medicament, i.e. a drug or other pharmaceutical agent.

The active agents that may be incorporated into the films of the present invention include, but are not limited to, pharmaceutical, cosmetic, cosmeceutical and nutraceutical actives. As used herein, a cosmeceutical refers to a product, which is a cosmetic, but which contains biologically active ingredients that have an effect on the user. A nutraceutical, as used herein, refers to a product isolated or purified from foods, and sold in medicinal forms not usually associated with food and demonstrated to have a physiological benefit or provide protection against disease. Examples of nutraceuticals include beta-carotene and lycopene.

As used herein, a topical agent pertains to an agent that may be applied to a particular surface area, such as, but not limited to, a certain area of the skin or mucosal tissue. The film is used as a delivery system to carry the topical active agent to a particular surface area in need thereof. Also as used herein, an orally administered agent is an agent that may be ingested by a user, i.e., through the oral cavity. Such orally administered agents may be absorbed into the body through one or more mucosal cavities (i.e., buccal or sublingual) or may be ingested through the stomach.

In some embodiments, the polymeric film desirably includes at least one water soluble polymer. In some other embodiments, the film includes a combination of both water soluble and water insoluble polymers. When wetted, the dry film product at least partially solubilizes. Contacting the film product of the present invention with a wetting agent permits the topical agent to be dissolved or dispersed out of the film. Particularly in the case of topical films, the dissolved or dispersed topical agent may then be easily applied to a particular surface area, such as a skin area or mucosal area. The wetting agent may be a polar solvent, such as water. In orally administered embodiments, for example, the wetting agent may be saliva.

The wetting agent may be placed on a substrate surface, including skin and wounds, and the film placed on the wetted surface. Alternatively, the film may be placed on the substrate surface, including skin and wounds, and subsequently hydrated.

The wetting agent may be dispensed from a container, the container being separate from or affixed to the film. For example, the container may be a pump bottle or sealed tube including the wetting agent.

Alternatively, the container may be a sealed, rupturable pouch including the wetting agent. Such a pouch may be separate from or affixed to the film. When the pouch is ruptured, the wetting agent may be brought into direct contact with the film to cause the topical agent to be dissolved out or dispersed out of the film, whereby the topical agent can be applied to the substrate surface.

The film may be interposed between a container including the solvent and a substrate surface, including skin and wounds. Alternatively, the film may be interposed between a container including the solvent and an applicator.

For example, in some embodiments, a system useful for applying a topical agent includes a water soluble polymeric film containing the topical agent, a solvent, which may be present in a container, and an applicator for applying the topical agent to the substrate surface. In some embodiments, the applicator is a sponge applicator. The film may be deposited on top of a wetted sponge applicator. Alternatively, the film may be deposited on top of a dry sponge applicator, which is subsequently wetted.

As further described below, in some embodiments, the method of making the films of the present invention involves combining a water soluble, saccharide-based polymer, a polar solvent and the topical agent to form a wet material or matrix with a non-self-aggregating uniform heterogeneity. In some embodiments, a blend of water soluble polymers is used, such as at least one saccharide-based polymer and polyethylene oxide. The wet material or matrix is then formed into a film and dried in a controlled manner. In some embodiments, the topical agent, when combined with the polymer and the polar solvent, is in the form of a liquid, a solid or a gel.

When a topical agent is combined with the water soluble polymer(s) in the solvent, the type of material that is formed depends on the solubilities of the topical agent and the polymer(s). If the agent and/or polymer(s) are soluble in the selected solvent, this may form a solution. However, if the components are not soluble, the material that is formed may be classified as an emulsion, a colloid, or a suspension.

Examples of suitable topical agents which may be included in the films of the present invention include, but are not limited to, body washing agents, hair styling agents, moisturizing agents, underarm deodorants and/or antiperspirants, shaving creams or gels, sunscreens, and insect repellants.

The topical agent may also be a protein and/or peptide. For example, in some embodiments, the topical agent may be collagen, elastin or a combination thereof.

With respect to some preferred medicinal agents for topical applications, these include, but are not limited to, acne medications, antibacterial agents (e.g., antibiotics), hormones, agents for preventing motion sickness, and anesthetics.

In some embodiments, an active agent in a nanoparticle size, such as less than about 500 nm, may be combined with a water-soluble polymer composition to form a self-supporting film in accordance with the present invention. In some other embodiments, a medicinal agent in a nanoparticle size, such as preferably less than about 200 nm, may be combined with a water-soluble polymer composition to form a self-supporting film in accordance with the present invention.

A wide variety of medicaments, bioactive active substances and pharmaceutical compositions may be included in the dosage forms of the present invention. Such medicaments, bioactive substances and pharmaceutical compositions may be useful as topically-administered dosages or as orally-ingestible dosages. Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, antinauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of medicating active ingredients contemplated for use in the present invention include antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include opiates and opiate derivatives, such as oxycodone (commercially available as Oxycontin®); ibuprofen (commercially available as Motrin®, Advil®, Motrin Children's®, Motrin IB®, Advil Children's®, Motrin Infants'®, Motrin Junior®, Ibu-2®, Proprinal®, Ibu-200®, Midol Cramp Formula®, Bufen®, Motrin Migraine Pain®, Addaprin® and Haltran®), aspirin (commercially available as Empirin®, Ecotrin®, Genuine Bayer®, and Halfprin®), acetaminophen (commercially available as Silapap Infant's®, Silapap Children's®, Tylenol®, Tylenol Children's®, Tylenol Extra Strength®, Tylenol Infants' Original®, Tylenol Infants'®, Tylenol Arthritis®, T-Painol®, Q-Pap®, Cetafen®, Dolono®, Tycolene®, APAP® and Aminofen®), and combinations thereof that may optionally include caffeine. Other pain relieving agents may be used in the present invention, including meperidine hydrochloride (commercially available as Demerol®), hydromorphone hydrochloride (commercially available as Dilaudid®), propoxyphene napsylate and acetaminophen (commercially available as Darvocet-N®), Fentanyl (commercially available as Duragesic® and Fentora®), sodium hyaluronate (commercially avialble as Euflexxa®), adalimumab (commercially available as Humira®), sumatriptan succinate (commercially available as Imitrex®), fentanyl iontophoretic (commercially available as Ionsys®), orphenadrine citrate (commercially available as Norgesic®), magnesium salicylate tetrahydrate (commercially available as Novasal®), oxymorphone hydrochloride (commercially available as Opana ER®), methocarbamol (commercially available as Robaxin®), carisoprodol (commercially available as Soma®), tramadol hydrochloride (commercially available as Ultracet® and Ultram®), morphine sulfate (commercially available as MS Contin®), metaxalone (commercially available as Skelaxin®), oxycodone hydrochloride (commercially available as OxyContin®), acetaminophen/oxycodone hydrochloride (commercially available as Percocet®), oxycodone/aspirin (commercially available as Percodan®), hydrocodone bitartrate/acetaminophen (commercially available as Vicodin®), hydrocodone bitartrate/ibuprofen (commercially available as Vicoprofen®), nepafenac (commercially available as Nevanac®), and pregabalin (commercially available as Lyrica®).

The present invention may further include agents such as NSAIDs, including etodolac (commercially available as Lodine®), ketorolac tromethamine (commercially available as Acular®), naproxen sodium (commercially available as Anaprox®, Naprosyn®), flurbiprofen (commercially available as Ansaid®), diclofenac sodium/misoprostol (commercially available as Arthrotec®), celecoxib (commercially available as Celebrex®), sulindac (commercially available as Clinoril®), oxaprozin (commercially available as Daypro®), piroxicam (commercially available as Feldene®), indomethacin (commercially available as Indocin®), meloxicam (commercially available as Mobic®), mefenamic acid (commercially available as Ponstel®), tolmetin sodium (commercially available as Tolectin®), choline magnesium trisalicylate (commercially available as Trilisate®), diclofenac sodium (commercially available as Voltaren®), and misoprostol (commercially available as Cytotec®). Opiate agonists and antagonists, such as buprenorphine and naloxone are further examples of drugs for use in the present invention.

Other preferred drugs for other preferred active ingredients for use in the present invention include anti-diarrheals such as loperamide (commercially available as Imodium ADC), Imotil®, Kaodene®, Imperim®, Diamode®, QC Anti-Diarrheal®, Health Care America Anti-Diarrheal®, Leader A-D®, and Imogen®), nitazoxanide (commercially available as Alinia®) and diphenoxylate hydrochloride/atropine sulfate (commercially available as Lomotil®), anti-histamines, anti-tussives, decongestants, vitamins, and breath fresheners. Common drugs used alone or in combination for colds, pain, fever, cough, congestion, runny nose and allergies, such as acetaminophen, ibuprofen, chlorpheniramine maleate, dextromethorphan, dextromethorphan HBr, phenylephrine HCl, pseudoephedrine HCl, diphenhydramine and combinations thereof, such as dextromethophan HBr and phenylephrine HCl (available as Triaminic®) may be included in the film compositions of the present invention.

Other active agents useful in the present invention include, but are not limited to alcohol dependence treatment, such as acamprosate calcium (commercially available as Campral®); Allergy treatment medications, such as promethazine hydrochloride (commercially available as Phenergan®), hydrocodone polistirex/chlorpheniramine polistirex (commercially available as Tussionex®), cetirizine hydrochloride (commercially available as Zyrtec®), cetirizine hydrochloride/pseudoephedrine hydrochloride (commercially available as Zyrtec-D®), promethazine hydrochloride/codeine phosphate (commercially available as Phenergan® with Codeine), pemirolast (commercially available as Alamast®), fexofenadine hydrochloride (commercially available as Allegra®), meclizine hydrochloride (commercially available as Antivert®), azelastine hydrochloride (commercially available as Astelin®), nizatidine (commercially available as Axid®), desloratadine (commercially available as Clarinex®), cromolyn sodium (commercially available as Crolom®), epinastine hydrochloride (commercially available as Elestat®), azelastine hydrochloride (commercially available as Optivar®), prednisolone sodium phosphate (commercially available as Orapred ODT®), olopatadine hydrochloride (commercially available as Patanol®), ketotifen fumarate (commercially available as Zaditor®), and montelukast sodium (commercially available as Singulair®); and anti-histamines such as diphenhydramine HCl (available as Benadryl®), loratadine (available as Claritin®), astemizole (available as Hismanal®), nabumetone (available as Relafen®), diphenhydramine HCL (available as TheraFlu®) and clemastine (available as Tavist®).

Films of the present invention may further include Alzheimer's treatment medications, such as tacrine hydrochloride (commercially available as Cognex®), galantamine (commercially available as Razadyne®), donepezil hydrochloride (commercially available as Aricept®), rivastigmine tartrate (commercially available as Exelon®), and memantine (commercially available as Namenda®); anemia medication, such as cyanocobalamin (commercially available as Nascobal®); anesthetics, such as antipyrine with benzocaine (commercially available as Auralgan®, Aurodex® and Auroto®); angina medication, such as amlodipine besylate (commercially available as Norvasc®), nitroglycerin (commercially available as Nitro-Bid®, Nitro-Dur®, Nitrolingual®, Nitrostat®, Transderm-Nitro®), isosorbide mononitrate (commercially available as Imdur®), and isosorbide dinitrate (commercially available as Isordil®); anti-tussives such as guaifensin; anti-Alzheimer's agents, such as nicergoline; and $Ca^H$-antagonists such as nifedipine (commercially available as Procardia® and Adalat®).

Actives useful in the present invention may also include anti-asthmatics, such as albuterol sulfate (commercially available as Proventil®), ipratropium bromide (commercially available as Atrovent®), salmeterol xinafoate (commercially available as Serevent®), zafirlukast (commercially available as Accolate®), flunisolide (commercially available as AeroBid®), metaproterenol sulfate (commercially available as Alupent®), albuterol inhalation (commercially available as Ventolin®), terbutaline sulfate (commercially available as Brethine®), formoterol (commercially available as Foradil®), cromolyn sodium (commercially available as Intal®), levalbuterol hydrochloride (commercially available as Xopenex®), zileuton (commercially available as Zyflo®), fluticasone propionate/salmeterol (commercially available as Advair®), albuterol sulfate/triamcinolone acetonide (commercially available as Azmacort®), dimethylxanthine (commercially available as Theophylline®), and beclomethasone (commercially available as Beclovent®, Beconase®, Qvar®, Vancenase®, Vanceril®); and antibacterial medications, such as trimethoprim/sulfamethoxazole (commercially available as Bactrim®), mupirocin (commercially available as Bactroban®), metronidazole (commercially available as Flagyl®), sulfisoxazole acetyl (commercially available as Gantrisin®), bismuth subsalicylate and metronidazole/tetracycline hydrochloride (commercially available as Helidac Therapy®), nitrofurantoin (commercially available as Macrodantin®), norfloxacin (commercially available as Noroxin®), erythromycin ethylsuccinate/Sulfisoxazole acetyl (commercially available as Pediazole®), and levofloxacin (commercially available as Levaquin®).

The present invention may further include one or more Antibiotics, including amoxicillin (commercially available as Amoxil®), ampicillin (commercially available as Omnipen®, Polycillin® and Principen®), amoxicillin/clavulanate potassium (commercially available as Augmentin®), moxifloxacin hydrochloride (commercially available as Avelox®), clarithromycin (commercially available as Biaxin®), ceftibuten (commercially available as Cedax®), cefuroxime axetil (commercially available as Ceftin®), cefprozil (commercially available as Cefzil®), ciprofloxacin hydrochloride (commercially available as Ciloxan® and Cipro®), clindamycin phosphate (commercially available as Cleocin T®), doxycycline hyclate (commercially available as Doryx®), dirithromycin (commercially available as Dynabac®), erythromycin (commercially available as E.E.S.®, E-Mycin®, Eryc®, Ery-Tab®, Erythrocin®, and PCE®), erythromycin topical (commercially available as A/T/SO, Erycette®, T-Stat®), gemifloxacin (commercially available as Factive®), ofloxacin (commercially known as Ocuflox®, Floxin®), telithromycin (commercially available as Ketek®), lomefloxacin hydrochloride (commercially available as Maxaquin®), minocycline hydrochloride (commercially available as Minocin®), fosfomycin tromethamine (commercially available as Monurol®), penicillin with potassium (commercially available as Penicillin VK®, Veetids®), trimethoprim (commercially available as Primsol®), ciprofloxacin hydrochloride (commercially available as Proquin XR®), rifampin, isoniazid and pyrazinamide (commercially available as Rifater®), cefditoren (commercially available as Spectracef®), cefixime (commercially available as Suprax®), tetracycline (commercially available as Achromycin V® and Sumycin®), tobramycin (commercially available as Tobrex®), rifaximin (commercially available as Xifaxan®), azithromycin (commercially available as Zithromax®), azithromycin suspension (commercially available as Zmax®), linezolid (commercially available as Zyvox®), benzoyl peroxide and clindamycin (commercially available as BenzaClin®), erythromycin and benzoyl peroxide (commercially available as Benzamycin®), ciprofloxacin and dexamethasone (commercially available as Ciprodex®), polymyxin B sulfate/neomycin sulfate/hydrocortisone (commercially available as Cortisporin®), colistin sulfate/neomycin sulfate/hydrocortisone acetate/thonzonium bromide (commercially available as Cortisporin-TC Otic®), cephalexin hydrochloride (commercially available as Keflex®), cefdinir (commercially available as Omnicef®), and gatifloxacin (commercially available as Zymar®).

Other useful actives include cancer treatment medications, including cyclophosphamide (commercially available as Cytoxan®), methotrexate (commercially available as Rheumatrex® and Trexal®), tamoxifen citrate (commercially available as Nolvadex®), and anastrozole (commercially available as Arimidex®); anti-coagulants, such as aspirin with extended-release dipyridamole (commercially available as Aggrenox®), warfarin sodium (commercially available as Coumadin®), dipyridamole (commercially available as Persantine®), and clopidogrel bisulfate (commercially available as Plavix®); antiemetics, such as graniestron hydrochloride (commercially available as Kytril®) and nabilone (commercially available as Cesamet®), trimethobenzamide hydrochloride (commercially available as Tigan®), and ondansetron hydrochloride (commercially available as Zofran®); anti-fungal treatment, such as ketoconazole (commercially available as Nizoral®), posaconazole (commercially available as Noxafil®), ciclopirox (commercially available as Penlac®), griseofulvin (commercially available as Gris-PEG®), oxiconazole nitrate (commercially available as Oxistat®), fluconazole (commercially available as Diflucan®), sertaconazole nitrate (commercially available as Ertaczo®), terbinafine hydrochloride (commercially available as Lamisil®), ciclopirox (commercially available as Loprox®), nystatin/triamcinolone acetonide (commercially available as Mycolog-II®), econazole nitrate (commercially available as Spectazole®), itraconazole (commercially available as Sporanox®), and terconazole (commercially available as Terazol®).

Active agents may further include anti-inflammatory medications, such as hydroxychloroquine sulfate (commercially available as Plaquenil®), fluticasone propionate (commercially available as Cutivate®), amcinonide (commercially available as Cyclocort®), methylprednisolone (commercially available as Medrol®), budesonide (commercially available as Entocort EC®), anakinra (commercially available as Kineret®), diflorasone diacetate (commercially available as Psorcon®), and etanercept (commercially available as Enbrel®); antispasmodic medication, such as phenobarbital/hyoscyamine sulfate/atropine sulfate/scopolamine hydrobromide (commercially available as Donnatal®); antiviral treatment, such as oseltamivir phosphate (commercially available as Tamiflu®); anti-parasites medication, including tinidazole (commercially available as Tindamax®); appetite treatment mediations, such as megestrol acetate (commercially available as Megace ESC), phentermine hydrochloride (commercially available as Adipex-P®), and diethylpropion hydrochloride (commercially available as Tenuate®); arthritis medications, including leflunomide (commercially available as Arava®); bladder control medication, such as trospium chloride (commercially available as Sanctura®), desmopressin acetate (commercially available as DDAVP®), tolterodine tartrate (commercially available as Detrol®), oxybutynin chloride (commercially available as Ditropan®), darifenacin (commercially available as Enablex®), and solifenacin succinate (commercially available as VESIcare®); blood vessel constrictors, such as methylergonovine maleate (commercially available as Methergine®); cholesterol lowering medication, including paricalcitol (commercially available as Altocor®), lovastatin, niacin (commercially available as Advicor®), colestipol hydrochloride (commercially available as Colestid®), rosuvastatin calcium (commercially available as Crestor®), fluvastatin sodium (commercially available as Lescol®), atorvastatin calcium (commercially available as Lipitor®), lovastatin (commercially available as Mevacor®), niacin (commercially available as Niaspan®), pravastatin sodium (commercially available as Pravachol®), pravastatin sodium with buffered aspirin (commercially available as Pravigard PAC®), cholestyramine (commercially available as Questran®), simvastatin and niacin (commercially available as Simcor®), atenolol, chlorthalidone (commercially available as Tenoretic®), atenolol (commercially available as Tenormin®), fenofibrate (commercially available as Tricor®), fenofibrate (commercially available as Triglide®), ezetimibe/simvastatin (commercially available as Vytorin®), colesevelam (commercially available as WelChol®), bisoprolol fumarate (commercially available as Zebeta®), ezetimibe (commercially available as Zetia®), bisoprolol fumarate/hydrochlorothiazide (commercially available as Ziac®), and simvastatin (commercially available as Zocor®).

The actives included herein may also include chronic kidney disease medication, such as paricalcitol (commercially available as Zemplar®); contraceptive agents, including etonogestrel (commercially available as Implanon®), norethindrone acetate, ethinyl estradiol (commercially available as Loestrin 24 FE®), ethinyl estradiol, norelgestromin (commercially available as Ortho Evra®), levonorgestrel (commercially available as Plan B®), levonorgestrel and ethinyl estradiol (commercially available as Preven®), levonorgestrel, ethinyl estradiol (commercially available as Seasonique®), and medroxyprogesterone acetate (commercially available as Depo-Provera®); COPD medication, such as arformoterol tartrate (commercially available as Brovana®) and ipratropium bromide, albuterol sulfate (commercially available as Combivent®); cough suppressants, including benzonatate (commercially available as Tessalon®), guaifenesin, codeine phosphate (commercially available as Tussi-Organidin NR®), and acetaminophen, codeine phosphate (commercially available as Tylenol with Codeine®); medication for the treatment of diabetes, including pioglitazone hydrochloride, metformin hydrochloride (commercially available as ACTOplus Met®), pioglitazone hydrochloride (commercially available as Actos®), glimepiride (commercially available as Amaryl®), rosiglitazone maleate, metformin hydrochloride (commercially available as Avandamet®), rosiglitazone maleate (commercially available as Avandaryl®), rosiglitazone maleate (commercially available as Avandia®), exenatide (commercially available as Byetta®), chlorpropamide (commercially available as Diabinese®), pioglitazone hydrochloride, glimepiride (commercially available as Duetact®), metformin hydrochloride (commercially available as Glucophage®), glipizide (commercially available as Glucotrol®), glyburide, metformin (commercially available as Glucovance®), metformin hydrochloride (commercially available as Glumetza®), sitagliptin (commercially available as Januvia®), detemir (commercially available as Levemir®), glipizide, metformin hydrochloride (commercially available as Metaglip®), glyburide (commercially available as Micronase®), repaglinide (commercially available as Prandin®), acarbose (commercially available as Precose®), nateglinide (commercially available as Starlix®), pramlintide acetate (commercially available as Symlin®), and tolazamide (commercially available as Tolinase®).

Other useful agents of the present invention may include digestive agents, such as sulfasalazine (commercially available as Azulfidine®), rabeprazole sodium (commercially available as AcipHex®), lubiprostone (commercially available as Amitiza®), dicyclomine hydrochloride (commercially available as Bentyl®), sucralfate (commercially available as Carafate®), lactulose (commercially available as Chronulac®), docusate (commercially available as Colace®), balsalazide disodium (commercially available as Colazal®), losartan potassium (commercially available as Cozaar®), olsalazine sodium (commercially available as Dipentum®), chlordiazepoxide hydrochloride, clidinium bromide (commercially available as Librax®), esomeprazole magnesium (commercially available as Nexium®), famotidine (commercially available as Pepcid®), lansoprazole (commercially available as Prevacid®), lansoprazole and naproxen (commercially available as Prevacid NapraPAC®), amoxicillin/clarithromycin/lansoprazole (commercially available as Prevpac®), omeprazole (commercially available as Prilosec®), pantoprazole sodium (commercially available as Protonix®), metoclopramide hydrochloride (commercially available as Reglan®), cimetidine (commercially available as Tagamet®), ranitidine hydrochloride (commercially available as Zantac®), and omeprazole, sodium bicarbonate (commercially available as Zegerid®); diuretics, including spironolactone, hydrochlorothiazide (commercially available as Aldactazide®), spironolactone (commercially available as Aldactone®). bumetanide (commercially available as Bumex®), torsemide (commercially available as Demadex®), chlorothiazide (commercially available as Diuril®), furosemide (commercially available as Lasix®), metolazone (commercially available as Zaroxolyn®), and hydrochlorothiazide, triamterene (commercially available as Dyazide®).

Agents useful herein may also include treatment for emphysema, such as tiotropium bromide (commercially available as Spiriva®); enema treatments, including aminosalicylic acid (commercially available as Mesalamine® and Rowasa®); epilepsy medications, including valproic acid (commercially available as Depakene®), felbamate (commercially available as Felbatol®), lamotrigine (commercially available as Lamictal®), primidone (commercially available as Mysoline®), oxcarbazepine (commercially available as Trileptal®), zonisamide (commercially available as Zonegran®), levetiracetam (commercially available as Keppra®), and phenytoin sodium (commercially available as Dilantin®).

Erectile dysfunction therapies useful herein include, but are not limited to, drugs for facilitating blood flow to the penis, and for effecting autonomic nervous activities, such as increasing parasympathetic (cholinergic) and decreasing sympathetic (adrenersic) activities. Useful agents for treatment of erectile dysfunction include, for example, those agents available as alprostadil (commercially available as Caverject®), tadalafil (commercially available as Cialis®), vardenafil (commercially available as Levitra®), apomorphine (commercially available as Uprima®), yohimbine hydrochloride (commercially available as Aphrodyne®, Yocon®), and sildenafil citrate (commercially available as Viagra®).

Agents useful herein may further include eye medications and treatment, such as dipivefrin hydrochloride (commercially available as Propine®), valganciclovir (commercially available as Valcyte®), bromfenac (commercially available as Xibrom®), fluorometholone (commercially available as FML®), pilocarpine hydrochloride (commercially available as Pilocar®), cyclosporine (commercially available as Restasis®), brimonidine tartrate (commercially available as Alphagan P®), dorzolamide hydrochloride/timolol maleate (commercially available as Cosopt®), bimatoprost (commercially available as Lumigan®), timolol maleate (available as Timoptic®), travoprost (commercially available as Travatan®), latanoprost (commercially available as Xalatan®), echothiophate iodide (commercially available as Phospholine Iodide®), and ranibizumab (commercially available as Lucentis®); fluid controllers, such as acetazolamide (commercially available as Diamox®); gallstone medications, including ursodiol (commercially available as Actigall®); medication for the treatment of gingivitis, including chlorhexidine gluconate (commercially available as Peridex®); headache medications, including butalbital/codeine phosphate/aspirin/caffeine (commercially available as Fiornal® with Codeine), naratriptan hydrochloride (commercially available as Amerge®), almotriptan (commercially available as Axert®), ergotamine tartrate/caffeine (commercially available as Cafergot®), butalbital/acetaminophen/caffeine (commercially available as Fioricet®), butalbital/aspirin/caffeine (commercially available as Fiorinal®), frovatriptan succinate (commercially available as Frova®), rizatriptan benzoate (commercially available as Maxalt®), isometheptene mucate/dichloralphenazone/acetaminophen (commercially available as Midrin®), dihydroergotamine mesylate (commercially available as Migranal®), eletriptan hydrobromide (commercially available as Relpax®), and zolmitriptan (commercially available as Zomig®); and heart treatments, including quinidine sulfate, isosorbide dinitrate/hydralazine hydrochloride (commercially available as BiDil®), digoxin (commercially available as Lanoxin®), flecainide acetate (commercially available as Tambocor®), mexiletine hydrochloride (commercially available as Mexitil®), disopyramide phosphate (commercially available as Norpace®), procainamide hydrochloride (commercially available as Procanbid®), and propafenone (commercially available as Rythmol®).

Other useful agents include hepatitis treatments, including entecavir (commercially available as Baraclude®), hepatitis B immune globulin (commercially available as HepaGam B®), and copegus/rebetol/ribasphere/vilona/virazole (commercially available as Ribavirin®); herpes treatments, including valacyclovir hydrochloride (commercially available as Valtrex®), penciclovir (commercially available as Denavir®), acyclovir (commercially available as Zovirax®), and famciclovir (commercially available as Famvir®); treatment for high blood pressure, including enalaprilat (available as Vasotec®), captopril (available as Capoten®) and lisinopril (available as Zestril®), verapamil hydrochloride (available as Calan®), ramipril (commercially available as Altace®), olmesartan medoxomil (commercially available as Benicar®), amlodipine/atorvastatin (commercially available as Caduet®), nicardipine hydrochloride (commercially available as Cardene®), diltiazem hydrochloride (commercially available as Cardizem®), quinapril hydrochloride (commercially available as Accupril®), quinapril hydrochloride/hydrochlorothiazide (commercially available as Accuretic®), perindopril erbumine (commercially available as Aceon®), candesartan cilexetil (commercially available as Atacand®), candesartan cilexetil/hydrochlorothiazide (commercially available as Atacand HCT®), irbesartan/hydrochlorothiazide (commercially available as Avalide®), irbesartan (commercially available as Avapro®), amlodipine besylate/olmesartan medoxomil (commercially available as Azor®), levobunolol hydrochloride (commercially available as Betagan®), betaxolol hydrochloride (commercially available as Betoptic®), nebivolol (commercially available as Bystolic®), captopril/hydrochlorothiazide (commercially available as Capozide®), doxazosin mesylate (commercially available as Cardura®), clonidine hydrochloride (commercially available as Catapres®), carvedilol (commercially available as Coreg®), nadolol (commercially available as Corgard®), nadolol/bendroflumethiazide (commercially available as Corzide®), valsartan (commercially available as Diovan®), isradipine (commercially available as DynaCirc®), wytensin. (commercially available as Guanabenz Acetate®), tenex (commercially available as Guanfacine Hydrochloride®), losartan potassium/hydrochlorothiazide (commercially available as Hyzaar®), propranolol hydrochloride (commercially available as Indera®), propranolol hydrochloride/hydrochlorothiazide (commercially available as Inderide®), eplerenone (commercially available as Inspra®), ambrisentan (commercially available as Letairis®), enalapril maleate/felodipine (commercially available as Lexxel®), metoprolol tartrate (commercially available as Lopressor®), benazepril hydrochloride (commercially available as Lotensin®), benazepril hydrochloride/hydrochlorothiazide (commercially available as Lotensin HCT®), amlodipine/benazepril hydrochloride (commercially available as Lotrel®), indapamide (commercially available as Lozol®), trandolapril (commercially available as Mavik®), telmisartan (commercially available as Micardis®), telmisartan/hydrochlorothiazide (commercially available as Micardis HCT®), prazosin hydrochloride (commercially available as Minipress®), amiloride, hydrochlorothiazide (commercially available as Moduretic®), fosinopril sodium (commercially available as ZZXT Monopril®), fosinopril sodium/hydrochlorothiazide (commercially available as Monopril-HCT®), pindolol (commercially available as Visken®), felodipine (commercially available as Plendil®), sildenafil citrate (commercially available as Revatio®), Nisoldipine (commercially available as Sular®), trandolapril/verapamil hydrochloride (commercially available as Tarka®), aliskiren (commercially available as Tekturna®), eprosartan mesylate (commercially available as Teveten®), eprosartan mesylate/hydrochlorothiazide (commercially available as Teveten HCT®), moexipril hydrochloride/hydrochlorothiazide (commercially available as Uniretic®), moexipril hydrochloride (commercially available as Univasc®), enalapril maleate/hydrochlorothiazide (commercially available as Vaseretic®), and lisinopril/hydrochlorothiazide (commercially available as Zestoretic®).

The present invention may include agents useful in the medication for the treatment of HIV/AIDS, such as amprenavir (commercially available as Agenerase®), tipranavir (commercially available as Aptivus®), efavirenz/emtricitabine/tenofovir (commercially available as Atripla®), lamivudine/zidovudine (commercially available as Combivir®), indinavir sulfate (commercially available as Crixivan®), lamivudine (commercially available as Epivir®), saquinavir (commercially available as Fortovase®), zalcitabine (commercially available as Hivid®), lopinavir/ritonavir (commercially available as Kaletra®), fosamprenavir calcium (commercially available as Lexiva®), ritonavir (commercially available as Norvir®), zidovudine (commercially available as Retrovir®), atazanavir sulfate (commercially available as Reyataz®), efavirenz (commercially available as Sustiva®), abacavir/lamivudine/zidovudine (commercially available as Trizivir®), didanosine (commercially available as Videx®), nelfinavir mesylate (commercially available as Viracept®), nevirapine (commercially available as Viramune®), tenofovir disoproxil fumarate (commercially available as Viread®), stavudine (commercially available as Zerit®), and abacavir sulfate (commercially available as Ziagen®); homocysteiene removers, including betaine anhydrous (commercially available as Cystadane®); medications, such as insulin (commercially available as Apidra®, Humalog®, Humulin®, Iletin®, and Novolin®); and HPV treatment, such as Human papillomavirus vaccine (commercially available as Gardasil®); immunosuppressants, including cyclosporine (commercially available asgENGRAF®, Neoral®, Sandimmune®, and Apo-Cyclosporine®).

Agents useful in the present invention may further include prolactin inhibitors, such as bromocriptine mesylate (commercially available as Parlodel®); medications for aiding in stress tests, such as regadenoson (commercially available as Lexiscan®); baldness medication, including finasteride (commercially available as Propecia® and Proscar®); pancreatitis treatment, such as gemfibrozil (commercially available as Lopid®); hormone medications, such as norethindrone acetate/ethinyl estradiol (commercially available as femHRT®), goserelin acetate (commercially available as Zoladex®), progesterone gel (commercially available as Prochieve®), progesterone (commercially available as Prometrium®), calcitonin-salmon (commercially available as Miacalcin®), calcitriol (commercially available as Rocaltrol®), synthroid (commercially available as Levothroid®, Levoxyl®, Unithroid®), testosterone (commercially available as Testopel®, Androderm®, Testoderm®, and AndroGel®); menopause medication, such as estradiol/norethindrone acetate (commercially available as Activella®), drospirenone/estradiol (commercially available as Angeliq®), estradiol/levonorgestrel (commercially available as Climara Pro®), estradiol/norethindrone acetate (commercially available as CombiPatch®), estradiol (commercially available as Estrasorb®, Vagifem® and EstroGel®), esterified estrogens and methyltestosterone (commercially available as Estratest®), estrogen (commercially available as Alora®, Climara®, Esclim®, Estraderm®, Vivelle®, Vivelle-Dot®), estropipate (commercially available as Ogen®), conjugated estrogens (commercially available as Premarin®), and medroxyprogesterone acetate (commercially available as Provera®); menstrual medications, including leuprolide acetate (commercially available as Lupron Depot), and norethindrone acetate (commercially available as Aygestin); and muscle relaxants, including cyclobenzaprine hydrochloride (commercially available as Flexeril®), tizanidine (commercially available as Zanaflex®), and hyoscyamine sulfate (commercially available as Levsin®).

Agents useful herein may also include osteoporosis medications, including ibrandronate sodium (commercially available as Boniva®), risedronate (commercially available as Actonel®), raloxifene hydrochloride (commercially available as Evista®, Fortical®), and alendronate sodium (commercially available as Fosamax®); ovulation enhancers, including clomiphene citrate (commercially available as Serophene®, Clomid®, Serophene®); Paget's disease treatment, such as etidronate disodium (commercially available as Didronel®); pancreatic enzyme deficiency medications, such as pancrelipase (commercially available as Pancrease®); medication for the treatment of Parkinson's disease, such as pramipexole dihydrochloride (commercially available as Mirapex®), ropinirole hydrochloride (commercially available as Requip®), carbidopa/levodopa (commercially available as Sinemet CR®), carbidopa/levodopa/entacapone (commercially available as Stalevo®), selegiline hydrochloride (commercially available as Zelapar®), rasagiline (commercially available as Azilect®), entacapone (commercially available as Comtan®), and selegiline hydrochloride (commercially available as Eldepryl®); prostate medication, including flutamide (commercially available as Eulexin®), nilutamide (commercially available as Nilandron®), dutasteride (commercially available as Avodart®), tamsulosin hydrochloride (commercially available as Flomax®), terazosin hydrochloride (commercially available as Hytrin®), and alfuzosin hydrochloride (commercially available as UroXatral®).

Films of the present invention may further include psychiatric medications, including alprazolam (available as Niravam®, Xanax®), clozopin (available as Clozaril®), haloperidol (available as Haldol®), fluoxetine hydrochloride (available as Prozac®), sertraline hydrochloride (available as Zoloft®), and paroxetine hydrochloride (available as Paxil®), aripiprazole (commercially aavialbe as Abilify®), Amphetamines and methamphetamines (commercially available as Adderall® and Desoxyn®), clomipramine hydrochloride (commercially available as Anafranil®), Buspirone hydrochloride (commercially available as BuSpar®), citalopram hydrobromide (commercially available as Celexa®), duloxetine hydrochloride (commercially available as Cymbalta®), methylphenidate (commercially available as Ritalin, Daytrana®), divalproex sodium (Valproic acid) (commercially available as Depakote®), dextroamphetamine sulfate (commercially available as Dexedrine®), venlafaxine hydrochloride (commercially available as Effexor®), selegiline (commercially available as Emsam®), carbamazepine (commercially available as Equetro®), lithium carbonate (commercially available as Eskalith®), fluvoxamine maleate/dexmethylphenidate hydrochloride (commercially available as Focalin®), ziprasidone hydrochloride (commercially available as Geodon®), ergoloid mesylates (commercially available as Hydergine®), escitalopram oxalate (commercially available as Lexapro®), chlordiazepoxide (commercially available as Librium®), molindone hydrochloride (commercially available as Moban®), phenelzine sulfate (commercially available as Nardil®), thiothixene (commercially available as Navane®), desipramine hydrochloride (commercially available as Norpramin®), benzodiazepines (such as those available as Oxazepam®), nortriptyline hydrochloride (commercially available as Pamelor®), tranylcypromine sulfate (commercially available as Parnate®), prochlorperazine, mirtazapine (commercially available as Remeron®), risperidone (commercially available as Risperdal®), quetiapine fumarate (commercially available as Seroquel®), doxepin hydrochloride (commercially available as Sinequan®), atomoxetine hydrochloride (commercially available as Strattera®), trimipramine maleate (commercially available as Surmontil®), olanzapine/fluoxetine hydrochloride (commercially available as Symbyax®), imipramine hydrochloride (commercially available as Tofranil®), protriptyline hydrochloride (commercially available as Vivactil®), bupropion hydrochloride (commercially available as Wellbutrin®, Wellbutrin SR®, and Wellbutrin XR®), and olanzapine (commercially available as Zyprexa®).

Agents useful herein may also include uric acid reduction treatment, including allopurinol (commercially available as Zyloprim®); seizure medications, including gabapentin (commercially available as Neurontin®), ethotoin (commercially available as Peganone®), and topiramate (commercially available as Topamax®); treatment for shingles, such as zoster vaccine live (commercially available as Zostavax®); skin care medications, including calcipotriene (commercially available as Dovonex®), isotretinoin (commercially available as Accutane®), hydrocortisone/iodoquinol (commercially available as Alcortin®), sulfacetamide sodium/sulfur (commercially available as Avar®), azelaic acid (commercially available as Azelex®, Finacea®), benzoyl peroxide (commercially available as Desquam-E®), adapalene (commercially available as Differin®), fluorouracil (commercially available as Efudex®), pimecrolimus (commercially available as Elidel®), topical erythromycin (commercially available as A/T/S®, Erycette®, T-Stat®), hydrocortisone (commercially available as Cetacort®, Hytone®, Nutracort®), metronidazole (commercially available as MetroGel®), doxycycline (commercially available as Oracea®), tretinoin (commercially available as Retin-A® and Renova®), mequinol/tretinoin (commercially available as Solagé®), acitretin (commercially available as Soriatane®), calcipotriene hydrate/betamethasone dipropionate (commercially available as Taclonex®), tazarotene (commercially available as Tazorac®), fluocinonide (commercially available as Vanos®), desonide (commercially available as Verdeso®), miconazole nitrate/Zinc oxide (commercially available as Vusion®), ketoconazole (commercially available as Xolegel®), and efalizumab (commercially available as Raptiva®).

Other agents useful herein may include Sleep disorder medications, including zaleplon (available as Sonata®) and eszopiclone (available as Lunesta®), zolpidem tartrate (commercially available as Ambien®, Ambien CR®), lorazepam (commercially available as Ativan®), flurazepam hydrochloride (commercially available as Dalmane®), triazolam (commercially available as Halcion®), clonazepam (commercially available as Klonopin®), barbituates, such as Phenobarbital®), Modafinil (commercially available as Provigil®), temazepam (commercially available as Restoril®), ramelteon (commercially available as Rozerem®), clorazepate dipotassium (commercially available as Tranxene®), diazepam (commercially available as Valium®), quazepam (commercially available as Doral®), and estazolam (commercially available as ProSom®); smoking cessation medications, such as varenicline (commercially available as Chantix®), nicotine, such as Nicotrol®, and bupropion hydrochloride (commercially available as Zyban®); and steroids, including alclometasone dipropionate (commercially available as Aclovate®), betamethasone dipropionate (commercially available as Diprolene®), mometasone furoate (commercially available as Elocon®), fluticasone (commercially available as Flonase®, Flovent®, Flovent Diskus®, Flovent Rotadisk®), fluocinonide (commercially available as Lidex®), mometasone furoate monohydrate (commercially available as Nasonex®), desoximetasone (commercially available as Topicort®), clotrimazole/betamethasone dipropionate (commercially available as Lotrisone®), prednisolone acetate (commercially available as Pred Forte®, Prednisone®, Budesonide Pulmicort®, Rhinocort Aqua®), prednisolone sodium phosphate (commercially available as Pediapred®), desonide (commercially available as Tridesilon®), and halobetasol propionate (commercially available as Ultravate®).

Films of the present invention may further include agents useful for thyroid disease treatment, such as hormones TC and TD (commercially available as Armour Thyroid®); potassium deficiency treatment, including potassium chloride (commercially available as Micro-K®); triglycerides regulators, including omega-3-acid ethyl esters (commercially available as Omacor®); urinary medication, such as phenazopyridine hydrochloride (commercially available as Pyridium®) and methenamine, methylene blue/phenyl salicylate/benzoic acid/atropine sulfate/hyoscyamine (commercially available as Urised®); prenatal vitamins (commercially available as Advanced Natalcare®, Materna®, Natalins®, Prenate Advance®); weight control medication, including orlistat (commercially available as Xenical®) and sibutramine hydrochloride (commercially available as Meridia®).

One particularly useful active for use in the present invention includes cyclosporine, which is an immunosuppressive agent, typically used in organ transplant patients. Cyclosporine is known to be quite insoluble in water. For this reason, it is currently known to prepare cyclosporine in an emulsified form, so as to increase its bioavailability. The present invention provides a dosage form including actives, such as cyclosporine, in a small-scale form, so as to increase its bioavailability. In one embodiment, the active may be stabilized in a small-scale form in combination with an additive, such as vitamin E TPGS, an amphiphilic additive. In addition to vitamin E TPGS, any other amphiphilic additives may be used, including but not limited to sodium dodecyl sulfate, benzalkonium chloride, cocamido propyl betaine, saponins, fatty acids, bile acids, and combinations thereof. The present invention is not limited to amphiphilic additives, and may include any solvent with the addition of a surface active agent.

Such small-scale particles may reduce the size of the active to as low as 1% its size in an unencumbered state (referred to herein as the "raw state"). In some embodiments, the small-scale particle may be about 5% the size of the active in its raw state, about 10% the size of the active in its raw state, about 15% the size of the active in its raw state, about 25% the size of the active in its raw state, or about 50% the size of the active in its raw state.

The popular $H_2$-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

An anti-oxidant may also be added to the film to prevent the degradation of an active, especially where the active is photosensitive.

Color additives can be used in preparing the films. Such color additives include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components.

Moreover, fragrances can be included in the films. These may include extracts derived from plants, leaves, flowers, fruits and combinations thereof, for example.

Films for Delivery of Small-Scale Actives

Films of the present invention may include small-scale forms of the active component to be delivered. As used herein, the term "small scale actives" includes actives in a small form, such as droplets and particles. One particularly useful form of the small-scale active is a small particle, such as a microparticle or nanoparticle as further defined herein. Other small-scale forms include microdroplets and nanodroplets. Such small-scale forms of actives may be formed through any desired means, including via emulsion technology, evaporation, precipitation, milling or any other desired means. In some embodiments, the small-scale active may be formed into a complex with another component, such as a ligand, for the purpose of maintaining the small size of the active during mixing with the polymeric matrix. The small-scale active may be chemically bound to another component or may be physically bound to the component.

Some of the aforementioned agents may be classified as emulsion compositions. An emulsion is typically a fluid consisting of a heterogeneous mixture of two normally immiscible liquid phases, in which one liquid forms droplets suspended in the other liquid. Emulsion compositions may include, but are not limited to, skin care creams, sunscreens, insect repellants, hair conditioners, hair styling agents (e.g., hair thickening agents), certain shampoos, and pharmaceutical ointments. Emulsions may additionally be used in orally-administered dosages. Such products are traditionally sold as liquids or semi-solids (e.g., ointments).

It has been discovered that liquid/liquid emulsions may be captured in a flowable film matrix, which when dried transforms the liquid/liquid emulsion into a liquid/solid emulsion. At least a portion of the water from the captured emulsion may be evaporated during the drying of the film. The resultant dried film product may be a solid film matrix having a plurality of discrete lipophilic droplets dispersed therein, the droplets being deposited from the liquid/liquid emulsion. The dried film, however, is readily rehydrated to dissolve the water soluble matrix and reform the emulsion by contacting the film with water. As used herein, the term "lipophilic" means having an affinity or attraction for lipids.

In some embodiments, the lipophilic droplets captured within the film during drying of the film may include therewithin drugs. When the dried film is rehydrated with water, a drug emulsion is formed, which may be topically applied.

In some embodiments, a method of preparing an emulsion composition in accordance with the present invention includes providing an aqueous-based emulsion; and converting the aqueous-based emulsion into a non-aqueous dry emulsion, wherein the dry emulsion is in the form of a self-supporting film. The method further includes dissolving the film with an aqueous solvent, thereby reforming the aqueous-based emulsion.

Where typical emulsions require a substantial amount of kinetic energy to "emulsify" the constituents, e.g., heavy mixing or shearing to form oil droplets in an aqueous medium, the invention provides a product which readily forms an emulsion upon contact with water, with very low energy input. Since the lipophilic droplets are already formed and suspended in the water soluble matrix, once the matrix is solubilized by contact with water, the liquid droplets readily become suspended in the surrounding water.

The lipophilic droplets are preferably microscopically discrete and distinct droplets that have an affinity for lipids. For example, the lipophilic droplets may be fat droplets, oil droplets, wax droplets, sterol droplets, glyceride droplets, or combinations thereof.

A film of the present invention may be formed by preparing a composition including at least one water soluble polymer, a polar solvent (e.g., water), and an emulsion composition. A film is then formed from the prepared composition, and the film is dried by a process whereby a plurality of lipophilic droplets become dispersed within the film. Suitable water soluble polymers for forming the film are the same as those described above. The emulsion composition employed to prepare the film may include an active, such that, during the drying process, a plurality of lipophilic droplets including the active become dispersed in the film. The emulsion, in effect, remains stable and intact during drying, and can be reconstituted when water is added back to dissolve the film. The reconstituted emulsion may then be administered to a user.

The small-scale form of the active agent may take one of many various forms. As will be described in more detail below, the small scale form may be in the form of a nanoparticle. Alternatively, the small scale form of the active may include liposomes, dendrimers, polymer nanoparticles and coated polymer-based nanoparticles, micelles, fullerenes, nanotubes, chitosan/lecithin nanoparticles, nanostructured biomaterials, stealth liposomes, nanocrystals, particles produced by homogenization and/or precipitation, nanoparticles with phospholipid-cation precipitates, calcium phosphate-based particles, albumin-bound particles, water/oil emulsions, and combinations thereof.

The films of the present invention are particularly well suited for delivery of small drug particles, such as nanoparticles. Nanoparticles are generally understood to be particles which have an average size of less than one micron. Typically this is an average diameter size. In some embodiments, the emulsions of the present invention include the drug particles, for example nanoparticles, to be captured within the lipophilic droplets which themselves are captured within the film and which when reconstituted with appropriate solvent, such as aqueous media, can be released. The presence of the active need not be limited, however, to the lipophilic droplets but can also be included in the matrix of the film. Additionally, one or more actives can be present and different actives may be included in a lipophilic droplet and concurrently in the film matrix.

In another aspect of the invention, liquid crystal structures, such those used in U.S. Pat. No. 5,891,845, which is herein incorporated in its entirety by reference, may be employed to deliver and/or control the release of drugs. These liquid crystal structures may be included in the films. Liquid crystal structures may include solid solutions of the drug and film. For example, such liquid crystal structures may include, for example, actives such as cyclosporine, nifedipine, diltiazem hydrochloride, and other related compounds. These actives form a solid solution when mixed with a surfactant, such as Vitamin E TPGS. The active/Vitamin E TPGS complex may be formed via any means, including heat-melting the components together to form a liquid crystal structure. The resulting composition is a small-scale, liquid crystal form of the active, which may be dispersed through a polymeric matrix as will be described in more detail below.

The small-scale active may be formed via any other desired means. For example, the small-scale form may be formed through microfluidics processing. In such processes, the small-scale active may include a nano-emulsion (or micro-emulsion). The microfluidic process may include the use of a high-energy device, such as a microfluidic pump. The pump is capable of colliding two streams of fluid into each other at high energy levels, forming an emulsion of the two fluids while also creating extremely small, fine droplet size. For example, the pump may generate a stream of solvent, such as water or other polar solvent, which is collided with a second stream, which may include an oil-based solvent with the active dissolved therein. The streams of fluid are desirably collided at high pressures, for example from about 3,000 to about 5,000 psi. Alternatively, the streams of fluid may be collided at pressures of at least 3,000 psi. The resultant fine droplets may be dispersed throughout a polymeric matrix as will be described in more detail below, and formed into a film for administration.

In another embodiment, the small-scale active may be formed through physical manipulation, such as milling or grinding. In such embodiments, the active may be formed into a powder, slurry, or any other form. The active may then be dispersed into water or other fluid. The suspended active agent may then be subjected to a physical manipulation, such as milling or grinding or other similar process, until a suspension of small-scale particles of the active agent remains. The small-scale active may then be collected and dispersed throughout a polymeric matrix as will be described in more detail below, and formed into a film for administration. In some embodiments, the small-scale active may be added to the polymeric matrix via deposition. That is, the small-scale active may be deposited onto one or more surfaces of the polymeric matrix. Optionally, the small-scale active may be dispersed throughout a polymeric matrix in addition to being deposited onto one or more surfaces of the polymeric matrix.

In still other embodiments of forming the small-scale active, the active may be heated to the point of melting and subjected to evaporation. Such methods of heating to melt the active may be found in Applicant's co-pending U.S. application Publication No. 2009/0104270, the contents of which are incorporated by reference herein in their entirety. The active may be dispersed into a heated solvent to the point of melting, and the solvent evaporated to leave a residue of small-scale form of active. The small-scale form of active may be collected and dispersed throughout a polymeric matrix as will be described in more detail below, and formed into a film for administration.

Once the small-scale form of the agent has been formed, through any desired process, the small-scale form of the agent may optionally be bound to one or more ligands prior to dispersion into the polymeric matrix. Any ligand material may be used, including metals such as gold, polymers such as polyethylene glycol, and the like. The agent may be chemically bound to the ligand or it may be physically bound to the ligand (such as through electrostatic binding). Associating the small-scale form of the agent with a ligand aids in sustaining the small-scale form of the agent during preparation and formation of the film dosage. The ligand is bound to the agent during the formation of the film, which restricts the ability of the particles of the agent to agglomerate and therefore become non-uniform. Once the film has been ingested or absorbed by the user, the ligand is released from the agent, allowing the small-scale form of the agent to be absorbed into the body.

The ligand may be exposed to any body cavity, so long as there is sufficient moisture present to release the ligand. For example, the ligand may be placed in the oral cavity of the user, using saliva to release the agent. The delivery may be buccal, sublingual, peroral, topical, or any other delivery means desired.

The small-scale form of the agent, whether bound to a ligand or free, may be dispensed into a film forming polymeric matrix. Desirably, the agent is dispensed into the matrix in such a fashion that the agent is substantially uniform in distribution throughout the polymeric matrix. The polymeric matrix may then be subjected to heat so as to rapidly form a visco-elastic mass, as explained above. One particularly desirable drying process is described herein. By rapidly forming the visco-elastic mass, the particles of the agent are effectively trapped in place, so as to avoid undesirable agglomeration and/or migration of particles, which would result in non-uniformity of content in the unit dosage film. The resulting film product has a substantially uniform distribution of a small-scale form of the agent and has a predictable uniformity of content per unit dosage, i.e., the film formed can be cut into individual doses and will have substantially the same active content per unit dose.

While not wishing to be bound by any one theory, it is believed that, in the present invention, the film rheology changes so quickly during drying that the emulsion, which typically will break when heated and water is evaporated, is in fact still intact. The emulsion characteristics are substantially maintained, even when all of the water is evaporated away during the film drying process. When water is added back to the film, the emulsion reforms, and can be delivered topically or orally.

In some embodiments, the drying process includes heating the film at a temperature above the phase inversion temperature of the emulsion composition. A phase inversion temperature for an emulsion is the temperature at which an emulsion will go from either a water/oil emulsion to an oil/water emulsion or vice versa. Typically, if one were to try to remove the water phase from an aqueous-based emulsion by drying, then one would expect the emulsion to turn into one phase (i.e., oil). However, by heating the film in accordance with the methods provided herein, the oil droplets are captured in the film before coalescence of the oil droplets can occur, thereby permitting the system to be stabilized at a higher energy state relative to that if the emulsion converted to just one phase in the absence of water. For example, in some embodiments, the film is heated at a temperature above the phase inversion temperature for the emulsion in order to capture a plurality of oil droplets in the film. In some other embodiments, the drying is performed for about 10 to about 15 minutes.

In the present invention, an emulsion may be prepared by providing a solid water soluble polymeric film having dispersed therein a plurality of the lipophilic droplets; and adding water to dissolve the film, thereby forming an emulsion. The emulsion may be applied to surface in need thereof, such as a body surface.

A further aspect of the present invention relates to a method of preparing a water reconsitutable emulsion composition. The method includes preparing a composition including at least one water soluble polymer; a polar solvent; and an emulsion composition. The method further includes drying the composition to form a dry emulsion including lipophilic droplets dispersed within a solid water soluble polymeric matrix. As described above, the drying process may include heating at a temperature above the critical inversion temperature of the emulsion. In some embodiments, the dry emulsion is formed by drying for about 10 to about 15 minutes.

In some embodiments, a system useful for applying an emulsion includes a dry emulsion including lipophilic droplets dispersed with a water soluble polymeric film; and a solvent for dissolving the polymeric film. The solvent is provided for direct contact with the dry emulsion to cause the dry emulsion to be reconstituted, whereby the reconstituted emulsion can be applied to the substrate surface, including skin and wounds. The solvent may be present in a container separate from or affixed to the film. Suitable containers include, but are not limited to, pump bottles, sealed tubes and sealed, rupturable pouches.

The system may optionally include an applicator for applying the reconstituted emulsion to the substrate surface. The applicator may, for example, be a sponge. In some embodiments, the film is deposited on top of a wetted sponge applicator. In some other embodiments, the film is deposited on top of a dry sponge applicator, which when subsequently wetted with the solvent, is used to apply the reconstituted emulsion.

The film may be interposed between a container including the solvent and an area of skin. Alternatively, the film may be interposed between a container including the solvent and an applicator, such as a sponge applicator.

In some embodiments, the films of the present invention are useful for delivering any biologically active compound, including, for example, a pharmaceutical, cosmetic, cosmeceutical or nutraceutical active. For example, the lipophilic droplets deposited from a liquid/liquid emulsion may contain any of the actives described herein, such as drugs, vitamins, minerals, medicinal agents, herbals, botanicals, animal extracts or products, cosmetic ingredients, cosmeceuticals or nutraceuticals. In some embodiments, the active is solubilized in the lipophilic droplets. In some other embodiments, the active is suspended in the lipophilic droplets.

Films for Delivery of Eutectic Compositions

The present invention also provides film compositions, which are useful for delivering a dispersion of a eutectic composition. The film composition includes a solid water soluble polymeric matrix; and a plurality of droplets of a eutectic composition dispersed within the matrix. The film composition forms a dispersion of the eutectic composition when exposed to water. As defined herein, a eutectic composition is a mixture of two or more components which has a lower melting point than any of its constituents.

In some embodiments, the eutectic composition is a mixture of prilocaine and lidocaine. It has been discovered that a eutectic composition can be formed in situ from lidocaine and the HCl salt of prilocaine, as shown in the examples below. In particular, the HCl salt of prilocaine was neutralized with sodium hydroxide in situ in order to obtain the prilocaine base needed to form the eutectic composition with lidocaine. The prilocaine/lidocaine eutectic was combined with a blend of polymers in the presence of water to produce a film containing a dispersion of the eutectic oil as observed under a microscope. When wetted, the film dissolved, and turned opaque, indicating that the eutectic oil was being released as small emulsion-type droplets.

Dosages

The film products of the present invention are capable of accommodating a wide range of amounts of the agent. The films are capable of providing an accurate dosage amount (determined by the size of the film and concentration of the agent in the original polymer/water combination) regardless of whether the required dosage is high or extremely low. Therefore, depending on the type of agent that is incorporated into the film, the agent amount may be as high as about 300 mg, desirably up to about 150 mg or as low as the microgram range, or any amount therebetween.

The film products and methods of the present invention are well suited for high potency, low dosage active agents. This is accomplished through the high degree of uniformity of the films. Therefore, low dosage drugs, particularly more potent racemic mixtures of actives are desirable.

Anti-Foaming and De-Foaming Compositions

Anti-foaming and/or de-foaming components may also be used with the films of the present invention. These components aid in the removal of air, such as entrapped air, from the film-forming compositions. As described above, such entrapped air may lead to non-uniform films. Simethicone is one particularly useful anti-foaming and/or de-foaming agent. The present invention, however, is not so limited and other anti-foam and/or de-foaming agents may suitable be used.

Simethicone is generally used in the medical field as a treatment for gas or colic in babies. Simethicone is a mixture of fully methylated linear siloxane polymers containing repeating units of polydimethylsiloxane which is stabilized with trimethylsiloxy end-blocking unites, and silicon dioxide. It usually contains 90.5-99% polymethylsiloxane and 4-7% silicon dioxide. The mixture is a gray, translucent, viscous fluid which is insoluble in water.

When dispersed in water, simethicone will spread across the surface, forming a thin film of low surface tension. In this way, simethicone reduces the surface tension of bubbles air located in the solution, such as foam bubbles, causing their collapse. The function of simethicone mimics the dual action of oil and alcohol in water. For example, in an oily solution any trapped air bubbles will ascend to the surface and dissipate more quickly and easily, because an oily liquid has a lighter density compared to a water solution. On the other hand, an alcohol/water mixture is known to lower water density as well as lower the water's surface tension. So, any air bubbles trapped inside this mixture solution will also be easily dissipated. Simethicone solution provides both of these advantages. It lowers the surface energy of any air bubbles that trapped inside the aqueous solution, as well as lowering the surface tension of the aqueous solution. As the result of this unique functionality, simethicone has an excellent anti-foaming property that can be used for physiological processes (anti-gas in stomach) as well as any for external processes that require the removal of air bubbles from a product.

In order to prevent the formation of air bubbles in the films of the present invention, the mixing step can be performed under vacuum. However, as soon as the mixing step is completed, and the film solution is returned to the normal atmosphere condition, air will be re-introduced into or contacted with the mixture. In many cases, tiny air bubbles will be again trapped inside this polymeric viscous solution. The incorporation of simethicone into the film-forming composition either substantially reduces or eliminates the formation of air bubbles.

Simethicone may be added to the film-forming mixture as an anti-foaming agent in an amount from about 0.01 weight percent to about 5.0 weight percent, more desirably from about 0.05 weight percent to about 2.5 weight percent, and most desirably from about 0.1 weight percent to about 1.0 weight percent.

Optional Components

A variety of other components and fillers may also be added to the films of the present invention. These may include, without limitation, surfactants; plasticizers which assist in compatibilizing the components within the mixture; polyalcohols; anti-foaming agents, such as silicone-containing compounds, which promote a smoother film surface by releasing oxygen from the film; and thermo-setting gels such as pectin, carageenan, and gelatin, which help in maintaining the dispersion of components.

The variety of additives that can be incorporated into the inventive compositions may provide a variety of different functions. Examples of classes of additives include excipients, lubricants, buffering agents, stabilizers, blowing agents, pigments, coloring agents, fillers, bulking agents, fragrances, release modifiers, adjuviants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added with the active ingredient(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water soluble polysaccharides such as alginates, carrageenans, guar gum, agar-agar, xanthan gum, gellan gum, gum arabic and related gums (gum ghatti, gum karaya, gum tragancanth), pectin, water soluble derivatives of cellulose: alkylcelluloses hydroxyalkylcelluloses and hydroxyalkylalkylcelluloses, such as methylcelulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water soluble chemical derivatives of starch, cationically modified acrylates and methacrylates possessing, for example, a tertiary or quaternary amino group, such as the diethylaminoethyl group, which may be quaternized if desired; and other similar polymers.

Such extenders may optionally be added in any desired amount desirably within the range of up to about 80%, desirably about 3% to 50% and more desirably within the range of 3% to 20% based on the weight of all components.

Further additives may be glidants and opacifiers, such as the oxides of magnesium aluminum, silicon, titanium, etc. desirably in a concentration range of about 0.02% to about 3% by weight and desirably about 0.02% to about 1% based on the weight of all components.

Further examples of additives are plasticizers which include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sorbitol, sodium diethylsulfosuccinate, triethyl citrate, tributyl citrate, and the like, added in concentrations ranging from about 0.5% to about 30%, and desirably ranging from about 0.5% to about 20% based on the weight of the polymer.

There may further be added compounds to improve the texture of the starch material such as animal or vegetable fats, desirably in their hydrogenated form, especially those which are solid at room temperature. These fats desirably have a melting point of 50° C. or higher. Preferred are tri-glycerides with $C_{12}$-, $C_{14}$-, $C_{16}$-, $C_{18}$-, $C_{20}$- and $C_{22}$-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with $C_{12}$-, $C_{14}$-, $C_{16}$-, $C_{18}$-, $C_{20}$- and $C_{22}$-fatty acids.

The total amounts used of the fats, mono-, di-glycerides and/or lecithins are up to about 5% and preferably within the range of about 0.5% to about 2% by weight of the total composition It is further useful to add silicon dioxide, calcium silicate, or titanium dioxide in a concentration of about 0.02% to about 1% by weight of the total composition. These compounds act as opacifiers and flow agents.

These additives are to be used in amounts sufficient to achieve their intended purpose. Generally, the combination of certain of these additives will alter the overall release profile of the active ingredient and can be used to modify, i.e. impede or accelerate the release.

Lecithin is one surface active agent for use in the present invention. Lecithin can be included in the feedstock in an amount of from about 0.25% to about 2.00% by weight. Other surface active agents, i.e. surfactants, include, but are not limited to, cetyl alcohol, sodium lauryl sulfate, the Spans™ and Tweens™ which are commercially available from ICI Americas, Inc. Ethoxylated oils, including ethoxylated castor oils, such as Cremophor® EL which is commercially available from BASF, are also useful. Carbowax™ is yet another modifier which is very useful in the present invention. Tweens™ or combinations of surface active agents may be used to achieve the desired hydrophilic-lipophilic balance ("HLB"). The present invention, however, does not require the use of a surfactant and films or film-forming compositions of the present invention may be essentially free of a surfactant while still providing the desirable uniformity features of the present invention.

As additional modifiers which enhance the procedure and product of the present invention are identified, Applicants intend to include all such additional modifiers within the scope of the invention claimed herein.

Other ingredients include binders which contribute to the ease of formation and general quality of the films. Non-limiting examples of binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.

Films of the present invention, particularly films useful for oral ingestion by a user, may further include one or more taste-enhancing agents, such as flavors and/or sweeteners. Suitable flavors and sweeteners include those set forth in U.S. Pat. No. 7,425,292, the entire contents of which are incorporated by reference herein.

Further potential additives include solubility enhancing agents, such as substances that form inclusion compounds with active components. Such agents may be useful in improving the properties of very insoluble and/or unstable actives. In general, these substances are doughnut-shaped molecules with hydrophobic internal cavities and hydrophilic exteriors. Insoluble and/or instable actives may fit within the hydrophobic cavity, thereby producing an inclusion complex, which is soluble in water. Accordingly, the formation of the inclusion complex permits very insoluble and/or instable actives to be dissolved in water. A particularly desirable example of such agents are cyclodextrins, which are cyclic carbohydrates derived from starch. Other similar substances, however, are considered well within the scope of the present invention.

Forming the Film

The films of the present invention must be formed into a sheet prior to drying. After the desired components are combined to form a multi-component matrix, including the polymer, water, and an active or other component as desired, the combination is formed into a sheet or film, by any method known in the art such as coating, spreading, casting or drawing the multi-component matrix. If a multi-layered film is desired, this may be accomplished by co-extruding more than one combination of components which may be of the same or different composition. A multi-layered film may also be achieved by coating, spreading, or casting a combination onto an already formed film layer.

Although a variety of different film-forming techniques may be used, it is desirable to select a method that will provide a flexible film, such as reverse roll coating. The flexibility of the film allows for the sheets of film to be rolled and transported for storage or prior to being cut into individual dosage forms. Desirably, the films will also be self-supporting or in other words able to maintain their integrity and structure in the absence of a separate support. Furthermore, the films of the present invention may be selected of materials that are edible or ingestible.

Casting the Film Composition

The invention uses processes for making self-supporting films having a substantially uniform distribution of components. The self supporting film is particularly useful for delivery of actives as discussed herein. The processes for making the film are designed to maintain the compositional uniformity of components distributed throughout the film, which is particularly necessary when actives, such as pharmaceutical actives, are incorporated into the film. In the pharmaceutical context, it is essential that the film is compositionally uniform so that it can be divided into individual film dosage units, each dosage unit having the appropriate amount of active when administered, such that regulatory approval can be secured.

One process used to make the films is described in U.S. application Ser. No. 10/074,272, which is incorporated in its entirety herein by reference. In this process, the films are prepared by rapidly forming a visco-elastic film by applying hot air currents to the film to prevent flow migration and intermolecular forces from creating aggregates or conglomerates thereby maintaining compositional uniform distribution of components in the film; and further drying the visco-elastic film to form a self-supporting film.

Desirably, the hot air currents are applied to the bottom of the film, with substantially no top air flow. This allows the depth of the film to be dried prior to forming a polymer skin on the top surface of the film, which would disrupt the surface of the film, leading to non-uniformity. The dried, self-supporting film is uniform in the distribution of the components contained therein, weight and thickness.

The film first may be fed onto the top side of a surface prior to the application of hot air currents. The wet film is desirably formed from a deaerated matrix within a time period before the active contained therein degrades. The hot air currents may then be applied to the bottom side of the surface with substantially no top air flow. The process may further include a step of dividing the dried film into individual dosage units of equal dimensions and compositional make-up. The hot air currents may be applied to the bottom surface of the film at a higher velocity than to the top surface of the film during drying. Hot air currents applied to dry the top of the films are less than that which would cause surface rippling or skinning This permits the film to sufficiently thicken in viscosity to lock-in volumetric uniformity while permitting evaporation of water through the non-skinned surface.

The process may further include the preliminary steps of forming a masterbatch premix of an edible water-soluble polymer and water; deaerating the premix by mixing; feeding a predetermining amount of the deaerated premix to at least one mixer; adding an active component to the mixer; and mixing the components to achieve a uniform distribution thereof. Thereafter, the wet film is formed and dried.

Coating or casting methods are particularly useful for the purpose of forming the films of the present invention. Specific examples include reverse roll coating, gravure coating, immersion or dip coating, metering rod or meyer bar coating, slot die or extrusion coating, gap or knife over roll coating, air knife coating, curtain coating, or combinations thereof, especially when a multi-layered film is desired.

Roll coating, or more specifically reverse roll coating, is particularly desired when forming films in accordance with the present invention. This procedure provides excellent control and uniformity of the resulting films, which is desired in the present invention. In this procedure, the coating material is measured onto the applicator roller by the precision setting of the gap between the upper metering roller and the application roller below it. The coating is transferred from the application roller to the substrate as it passes around the support roller adjacent to the application roller. Both three roll and four roll processes are common.

The gravure coating process relies on an engraved roller running in a coating bath, which fills the engraved dots or lines of the roller with the coating material. The excess coating on the roller is wiped off by a doctor blade and the coating is then deposited onto the substrate as it passes between the engraved roller and a pressure roller.

Offset Gravure is common, where the coating is deposited on an intermediate roller before transfer to the substrate.

In the simple process of immersion or dip coating, the substrate is dipped into a bath of the coating, which is normally of a low viscosity to enable the coating to run back into the bath as the substrate emerges.

In the metering rod coating process, an excess of the coating is deposited onto the substrate as it passes over the bath roller. The wire-wound metering rod, sometimes known as a Meyer Bar, allows the desired quantity of the coating to remain on the substrate. The quantity is determined by the diameter of the wire used on the rod.

In the slot die process, the coating is squeezed out by gravity or under pressure through a slot and onto the substrate. If the coating is 100% solids, the process is termed "Extrusion" and in this case, the line speed is frequently much faster than the speed of the extrusion. This enables coatings to be considerably thinner than the width of the slot.

The gap or knife over roll process relies on a coating being applied to the substrate which then passes through a "gap" between a "knife" and a support roller. As the coating and substrate pass through, the excess is scraped off.

Air knife coating is where the coating is applied to the substrate and the excess is "blown off" by a powerful jet from the air knife. This procedure is useful for aqueous coatings.

In the curtain coating process, a bath with a slot in the base allows a continuous curtain of the coating to fall into the gap between two conveyors. The object to be coated is passed along the conveyor at a controlled speed and so receives the coating on its upper face.

Drying the Film

The drying step is also a contributing factor with regard to maintaining the uniformity of the film composition. A controlled drying process is particularly important when, in the absence of a viscosity increasing composition or a composition in which the viscosity is controlled, for example by the selection of the polymer, the components within the film may have an increased tendency to aggregate or conglomerate. An alternative method of forming a film with an accurate dosage, that would not necessitate the controlled drying process, would be to cast the films on a predetermined well. With this method, although the components may aggregate, this will not result in the migration of the active to an adjacent dosage form, since each well may define the dosage unit per se.

When a controlled or rapid drying process is desired, this may be through a variety of methods. A variety of methods may be used including those that require the application of heat. The liquid carriers are removed from the film in a manner such that the uniformity, or more specifically, the non-self-aggregating uniform heterogeneity, that is obtained in the wet film is maintained.

Desirably, the film is dried from the bottom of the film to the top of the film. Desirably, substantially no air flow is present across the top of the film during its initial setting period, during which a solid, visco-elastic structure is formed.

This can take place within the first few minutes, e.g. about the first 0.5 to about 4.0 minutes of the drying process. Controlling the drying in this manner, prevents the destruction and reformation of the film's top surface, which results from conventional drying methods. This is accomplished by forming the film and placing it on the top side of a surface having top and bottom sides. Then, heat is initially applied to the bottom side of the film to provide the necessary energy to evaporate or otherwise remove the liquid carrier. The films dried in this manner dry more quickly and evenly as compared to air-dried films, or those dried by conventional drying means. In contrast to an air-dried film that dries first at the top and edges, the films dried by applying heat to the bottom dry simultaneously at the center as well as at the edges. This also prevents settling of ingredients that occurs with films dried by conventional means.

The temperature at which the films are dried is about 100° C. or less, desirably about 90° C. or less, and most desirably about 80° C. or less.

In some embodiments, the weight of the polar solvent is at least about 30% of the film before drying. In some other embodiments, the drying of the film reduces the weight percent of the polar solvent to about 10% or less. Preferably, the drying occurs within about 10 minutes or fewer.

Another method of controlling the drying process, which may be used alone or in combination with other controlled methods as disclosed above includes controlling and modifying the humidity within the drying apparatus where the film is being dried. In this manner, the premature drying of the top surface of the film is avoided.

Additionally, it has also been discovered that the length of drying time can be properly controlled, i.e. balanced with the heat sensitivity and volatility of the components, and particularly the flavor oils and drugs. The amount of energy, temperature and length and speed of the conveyor can be balanced to accommodate such actives and to minimize loss, degradation or ineffectiveness in the final film.

A specific example of an appropriate drying method is that disclosed by Magoon. Magoon is specifically directed toward a method of drying fruit pulp. However, the present inventors have adapted this process toward the preparation of thin films.

The method and apparatus of Magoon are based on an interesting property of water. Although water transmits energy by conduction and convection both within and to its surroundings, water only radiates energy within and to water. Therefore, the apparatus of Magoon includes a surface onto which the fruit pulp is placed that is transparent to infrared radiation. The underside of the surface is in contact with a temperature controlled water bath. The water bath temperature is desirably controlled at a temperature slightly below the boiling temperature of water. When the wet fruit pulp is placed on the surface of the apparatus, this creates a "refractance window." This means that infrared energy is permitted to radiate through the surface only to the area on the surface occupied by the fruit pulp, and only until the fruit pulp is dry. The apparatus of Magoon provides the films of the present invention with an efficient drying time reducing the instance of aggregation of the components of the film.

Another method of controlling the drying process involves a zone drying procedure. A zone drying apparatus may include a continuous belt drying tunnel having one or more drying zones located within. The conditions of each drying zone may vary, for example, temperature and humidity may be selectively chosen. It may be desirable to sequentially order the zones to provide a stepped up drying effect.

The speed of the zone drying conveyor desirably is continuous. Alternatively, the speed may be altered at a particular stage of the drying procedure to increase or decrease exposure of the film to the conditions of the desired zone. Whether continuous or modified, the zone drying dries the film without surface skinning.

Figure 9:
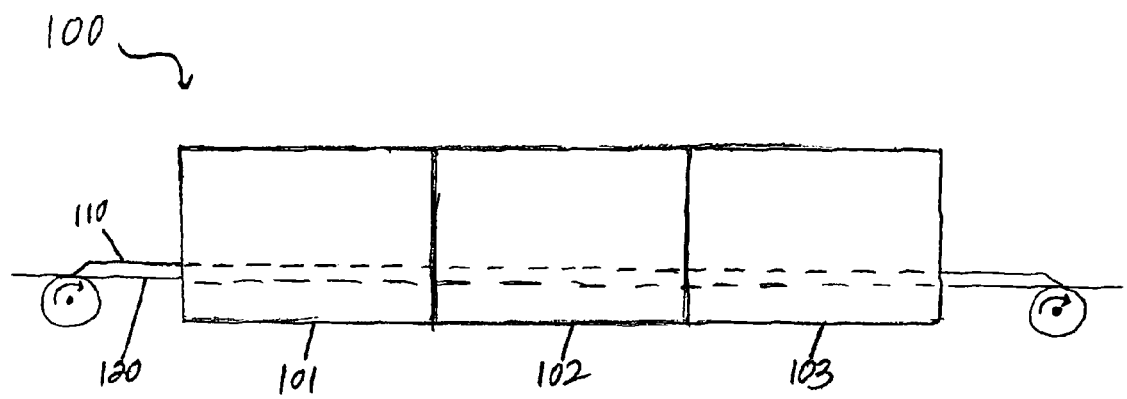
FIG. 9 is a schematic representation of a continuously-linked zone drying apparatus in accordance with the present invention.
Figure 10:
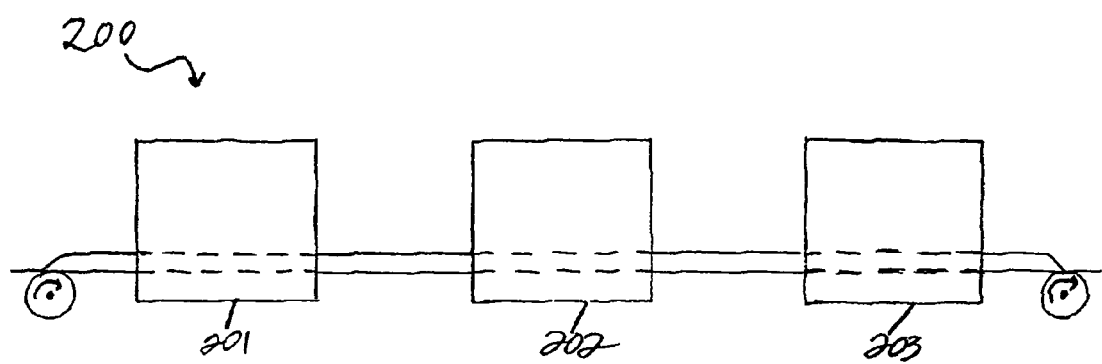
FIG. 10 is a schematic representation of a separate zone drying apparatus in accordance with the present invention.

According to an embodiment of the zone drying apparatus 100, shown in FIG. 9, the film 110 may be fed onto the continuous belt 120, which carries the film through the different drying zones. The first drying zone that the film travels through 101 may be a warm and humid zone. The second zone 102 may be hotter and drier, and the third zone 103 may also be hot and dry. These different zones may be continuous, or alternatively, they may be separated, as depicted by the zone drying apparatus 200 in FIG. 10, where the first drying zone 201, second drying zone 202 and third drying zone 203 are shown. The zone drying apparatus, in accordance with the present invention, is not limited to three drying zones. The film may travel through lesser or additional drying zones of varying heat and humidity levels, if desired, to produce the controlled drying effect of the present invention.

To further control temperature and humidity, the drying zones may include additional atmospheric conditions, such as inert gases. The zone drying apparatus further may be adapted to include additional processes during the zone drying procedure, such as, for example, spraying and laminating processes, so long as controlled drying is maintained in accordance with the invention.

The films may initially have a thickness of about 500 µm to about 1,500 µm, or about 20 mils to about 60 mils, and when dried have a thickness from about 3 µm to about 250 µm, or about 0.1 mils to about 10 mils. In some embodiments, the film product has a thickness of greater than 0.1 mils. In some other embodiments, the film product has a thickness of about 10 mils or fewer. In some further embodiments, the film product has a thickness of about 0.5 mils to about 5 mils. Desirably, the dried films will have a thickness of about 2 mils to about 8 mils, and more desirably, from about 3 mils to about 6 mils.

Testing Films for Uniformity

It may be desirable to test the films of the present invention for chemical and physical uniformity during the film manufacturing process. In particular, samples of the film may be removed and tested for uniformity in film components between various samples. Film thickness and overall appearance may also be checked for uniformity. Uniform films are desired, particularly for films containing pharmaceutical active components for safety and efficacy reasons.

A method for testing uniformity in accordance with the present invention includes conveying a film through a manufacturing process. This process may include subjecting the film to drying processes, dividing the film into individual dosage units, and/or packaging the dosages, among others. As the film is conveyed through the manufacturing process, for example on a conveyor belt apparatus, it is cut widthwise into at least one portion. The at least one portion has opposing ends that are separate from any other film portion. For instance, if the film is a roll, it may be cut into separate sub-rolls. Cutting the film may be accomplished by a variety of methods, such as with a knife, razor, laser, or any other suitable means for cutting a film.

The cut film then may be sampled by removing small pieces from each of the opposed ends of the portion(s), without disrupting the middle of the portion(s). Leaving the middle section intact permits the predominant portion of the film to proceed through the manufacturing process without interrupting the conformity of the film and creating sample-inducted gaps in the film. Accordingly, the concern of missing doses is alleviated as the film is further processed, e.g., packaged. Moreover, maintaining the completeness of cut portions or sub-rolls throughout the process will help to alleviate the possibility of interruptions in further film processing or packaging due to guilty control issues, for example, alarm stoppage due to notice of missing pieces.

After the end pieces, or sampling sections, are removed from the film portion(s), they may be tested for uniformity in the content of components between samples. Any conventional means for examining and testing the film pieces may be employed, such as, for example, visual inspection, use of analytical equipment, and any other suitable means known to those skilled in the art. If the testing results show non-uniformity between film samples, the manufacturing process may be altered. This can save time and expense because the process may be altered prior to completing an entire manufacturing run. For example, the drying conditions, mixing conditions, compositional components and/or film viscosity may be changed. Altering the drying conditions may involve changing the temperature, drying time, moisture level, and dryer positioning, among others.

Moreover, it may be desirable to repeat the steps of sampling and testing throughout the manufacturing process. Testing at multiple intervals may ensure that uniform film dosages are continuously produced. Alterations to the process can be implemented at any stage to minimize non-uniformity between samples.

Uses of Thin Films

The thin films of the present invention are well suited for many uses. The high degree of uniformity of the components of the film makes them particularly well suited for incorporating pharmaceuticals. Furthermore, the polymers used in construction of the films may be chosen to allow for a range of disintegration times for the films. A variation or extension in the time over which a film will disintegrate may achieve control over the rate that the active is released, which may allow for a sustained release delivery system. In addition, the films may be used for the administration of an active to skin and other body surfaces, including those with mucous membranes.

The films may be used to topically administer an active agent or may be used to orally administer the active agent. Topical administration may be accomplished by preparing the film as described above, introducing the film to a skin surface of a mammal, and wetting the film if necessary, for example. If desired, this film may be prepared and adhered to a second or support layer from which it is removed prior to use, i.e. application to the skin. An adhesive may be used to attach the film to the support or backing material, which may be any of those known in the art, and is preferably not water soluble. If an adhesive is used, it will desirably be an adhesive that does not alter the properties of the active. Mucoadhesive compositions are also useful. The film compositions in many cases serve as mucoadhesives themselves.

The films of the present invention take advantage of the films' tendency to dissolve quickly when wetted, i.e., through contact with a wetting agent such as water or saliva. An active may be introduced to a liquid by preparing a film in accordance with the present invention, introducing it to a liquid, and allowing it to dissolve. This may be used to prepare a liquid dosage form of an active, which may then be administered to the user.

A specific film shape or size may be preferred. Therefore, the film may be cut to any desired shape or size.

Figure 2:
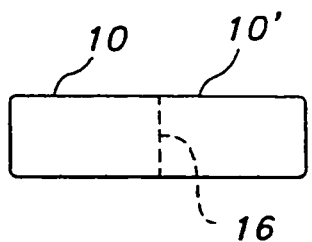
FIG. 2 shows a top view of two adjacently coupled packages containing individual unit dosage forms of the present invention, separated by a tearable perforation.
Figure 3:
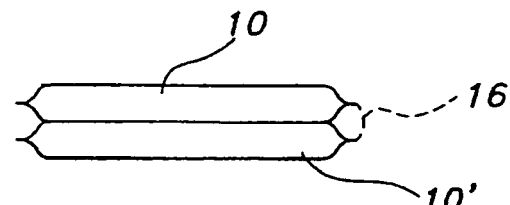
FIG. 3 shows a side view of the adjacently coupled packages of FIG. 2 arranged in a stacked configuration.
Figure 4:
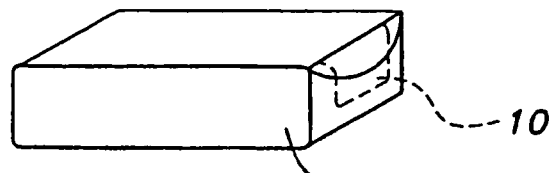
FIG. 4 shows a perspective view of a dispenser for dispensing the packaged unit dosage forms, dispenser containing the packaged unit dosage forms in a stacked configuration.
Figure 5:
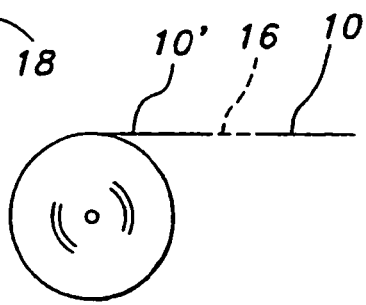
FIG. 5 is a schematic view of a roll of coupled unit dose packages of the present invention.

The films of the present invention are desirably packaged in sealed, air and moisture resistant packages to protect the active from exposure oxidation, hydrolysis, volatilization and interaction with the environment. Referring to FIG. 1, a packaged pharmaceutical dosage unit 10, such as a medicinal agent, is shown. Dosage unit 10 includes each film 12 individually wrapped in a pouch or between foil and/or plastic laminate sheets 14. As depicted in FIG. 2, the pouches 10, 10' can be linked together with tearable or perforated joints 16. The pouches 10, 10' may be packaged in a roll as depicted in FIG. 5 or stacked as shown in FIG. 3 and sold in a dispenser 18 as shown in FIG. 4. The dispenser may contain a full supply of the medication typically prescribed for the intended therapy, but due to the thinness of the film and package, is smaller and more convenient than traditional bottles used for tablets, capsules and liquids.

The films of the present invention dissolve instantly with a wetting agent, such as water, or by contact with mucosal membrane areas, such as found in the oral, anal or vaginal cavities. A wetting agent permits an active agent contained within the film to be dissolved or dispersed out of the film. In instances where the active agent is a topical agent, wetting the topical agent allows the topical agent to be easily applied to the skin or other particular surface area.

Desirably, a series of such unit doses are packaged together in accordance with the prescribed regimen or treatment, e.g., a 10-90 day supply, depending on the particular therapy. The individual films can be packaged on a backing and peeled off for use.

The features and advantages of the present invention are more fully shown by the following examples which are provided for purposes of illustration, and are not to be construed as limiting the invention in any way.

EXAMPLES

Example 1

Incorporation of a Skin Care Cream into a Film Base

The present example is directed to the incorporation of a skin care cream into a polyethylene oxide/hydroxypropylmethyl cellulose (70/30) film base. The skin care cream used in this example is an emulsion composition. The resulting film was found to be useful as a dissolvable skin lotion film (22.38% solids, by weight). The components are shown below in Table A.

TABLE A

| Components | Wt (g) |
| --- | --- |
| Polyethylene oxide WSR-N80 | 4.73 |
| Hydroxypropylmethyl cellulose E15 | 2.03 |
| Skin care cream[1] | 3.35 |
| Sorbitan monooleate NF (Span 80)[2] | 0.04 |

[1]Available from Stockhausen, and containing 2.15 g of three ingredients and 1.2 g water.
[2]Available from Farma International, Coral Gables, Florida.

The skin care cream and sorbitan monooleate from Table A were combined with 29.85 g of distilled water, and added to a Degussa 1100 bowl. Then, a blend of the polyethylene oxide and hydroxypropylmethyl cellulose (Table A) was added to the bowl. The combination of components was mixed using the Degussa Dental Multivac Compact. In particular, a solution was prepared by mixing the components at 125 rpm for preset time intervals under increasing vacuum as set forth in Table B below.

TABLE B

| Time (min) | Mixing Speed (rpm) | Vacuum (Hg) |
|---|---|---|
| 20 | 125 | 17 |
| 20 | 125 | 24 |
| 12 | 125 | 26.5 |
| 8 | 125 | 28 |

The solution was cast into film using the K-Control Coater with the micrometer adjustable wedge bar set at 450 microns onto the HDP side of 6330, coated side of 6330 and 55 # PS/1/5 "IN" release paper (tariff, Fallsington, Pa.). The film was dried 15 minutes in an 80° C. air oven to about 3.50% moisture (HR 73 Moisture Analyzer). The film released readily from all substrates.

The resulting film had a thickness of 2.8 mils, had good tear resistance, had sufficient strength when pulled, was not sticky, and passed the 180° bend test out of the moisture analyzer.

A piece of the film, when wetted in the hand with water, dissolved readily, leaving the skin care cream which spread on the skin easily. The emulsion reformed when the film was contacted with water.

The present example demonstrates the feasibility of preparing a dissolvable skin lotion film. The film was cut into 1½ inch by 2½ inch strips, which each weighed 148 mg, demonstrating the uniformity of the composition of the film.

Example 2

Incorporation of a Sunscreen into a Film Base

The present example is directed to the incorporation of a sunscreen into a polyethylene oxide/hydroxypropylmethyl cellulose (70/30) film base. The sunscreen used in this example is an emulsion composition. The resulting film was found to be useful as a dissolvable sunscreen lotion film (22% solids, by weight). The components of the film are shown below in Table C.

TABLE C

| Components | Wt (g) |
|---|---|
| Polyethylene oxide WSR-N80 | 4.90 |
| Hydroxypropylmethyl cellulose | 2.10 |
| Sunscreen[3] | 1.92 |
| Sorbitan monooleate NF (Span 80) | 0.044 |

[3]Blue Lizard sunscreen containing: 1.76 g (20%) active and other ingredients; and 0.16 g water.

The sunscreen and sorbitan monooleate from Table C were combined with 31.04 g of distilled water and added to a Degussa 1100 bowl. Then, a blend of the polyethylene oxide and hydroxypropylmethyl cellulose was added to the bowl. The combination of components was mixed using the Degussa Dental Multivac Compact under the same conditions as described in Table B of Example 1.

The resulting solution was cast into film using the K-Control Coater with the micrometer adjustable wedge bar set at 450 microns onto the HDP side of 6330. The film was dried 15 minutes in an 80° C. air oven. The film had 2.94% of moisture (HR73 Moisture Analyzer).

The resulting film had a thickness of 3 mil, showed some mottling on surface, showed curling, had good tear resistance and had a film adhesion rating of 5 from the HDP side of 6330. It also had sufficient strength when pulled, was not sticky and passed the 180° bend test out of the moisture analyzer. The film was cut into 1½ inch by 2½ inch pieces, each weighting 152 mg.

A piece of the film, when wetted in the hand, dissolved readily and left the sunscreen, which spread on the skin easily. In particular, the sunscreen emulsion reformed when the film was dissolved with water.

Example 3

Incorporation of an Antibacterial Hand Soap into a Film Base

The present example is directed to the incorporation of an antibacterial soap (Equate brand) into a polyethylene oxide/hydroxypropylmethyl cellulose (70/30) film base for use as a dissolvable soap film (22% solids, by weight). The components of the film are shown below in Table D.

TABLE D

| Components | Wt (g) |
|---|---|
| Polyethylene oxide WSR-N80 | 5.21 |
| Hydroxypropylmethyl cellulose E15 | 2.23 |
| Liquid antibacterial soap[4] | 9.62 |
| Sorbitan monooleate NF (Span 80) | 0.044 |

[4]Equate brand containing: 1.32 g (15%) active and other ingredients; and 8.3 g water.

The antibacterial soap and sorbitan monooleate were combined with 22.9 g distilled water in a Degussa 1100 bowl. Then, a blend of the polyethylene oxide and hydroxypropylmethyl cellulose was added to the bowl. The combination of components was mixed using the Degussa Dental Multivac Compact under the conditions set forth in Table E below.

TABLE E

| Time (min) | Mixing Speed (rpm) | Vacuum (Hg) |
|---|---|---|
| 20 | 100 | 17 |
| 20 | 100 | 19.75 |
| 12 | 100 | 22 |
| 8 | 100 | 25 |

The resulting solution was cast into film using the K-Control Coater with micrometer adjustable wedge bar set at 450 microns onto the HDP side of 6330, coated side of 6330, and 55 # PS/1/5 "IN" release paper (Griff). The film was dried 15 minutes in an 80° C. air oven to about 1.60% moisture (HR73 Moisture Analyzer).

The resulting film had a thickness of 4.5 mils, had a film adhesion rating of 6 from HDP side of 6330 and came loose from all substrates. It also had moderate tear resistance, had adequate strength when pulled, was not sticky, and passed the 180° bend test out of the moisture analyzer. A 1½ inch×2½ inch piece of film weighed 150 mg.

A piece of film, when wetted in the hand, dissolved fairly well, and left the soap which lathered on the skin.

Example 4

Incorporation of a Further Antibacterial Hand Soap into a Film Base

The present example is directed to incorporation of an antibacterial hand soap into a polyethylene oxide/hydroxypropylmethyl cellulose (70/30) film base. The film is to be used as a dissolvable hand soap film (22% solids, by weight).

The components of the film are shown below in Table F.

TABLE F

| Components | Wt (g) |
|---|---|
| Polyethylene oxide WSR-N80 | 4.87 |
| Hydroxypropylmethyl cellulose E15 | 2.08 |
| Antibacterial Hand Soap[8] | 2.86 |
| Menthol | .09 |

[7]Ultra Dawn Antibacterial Hand Soap containing: 1.76 g (20%) of active and other ingredients; and 1.1 g water.

The menthol and 30.1 g of distilled water were placed in a Degussa 1100 bowl. Then, a blend of the polyethylene oxide and hydroxypropylmethyl cellulose was added to the bowl.

A solution was prepared as described in Table G using the Degussa Dental Multivac Compact.

TABLE G

| Time (min) | Mixing Speed (rpm) | Vacuum (Hg) |
|---|---|---|
| 20 | 125 | 17 |
| 20 | 100 | 24 |
| 12 | 100 | 26.5 |
| 4 | 100 | 28 |

After 4 minute mixing interval shown in Table G, the antibacterial hand soap was added, and mixing continued for an additional four minutes at 100 rpm under vacuum at 28 Hg.

The resulting solution was cast into film using the K-Control Coater with the micrometer adjustable wedge bar set at 450 microns onto the HDP side of 6330, and coated side of 6330. The film was dried for 15 minutes in an 80° C. air oven. The percent moisture of the film was 2.6% (HR73 Moisture Analyzer).

The film had a thickness of 3 mils, came loose from both substrates, had a film adhesion rating of 5 from HDP side of 6330 and had moderate tear resistance. It also had good strength when pulled, was not sticky, and passed the 180° bend test out of the moisture analyzer. A 1½ inch 2½ inch strip weighed 153 mg.

When wetted in the hands, the film lumped up, indicating that a different film base would be needed for hand soap.

Example 5

Incorporation of an Anesthetic into a Film Base

The present example is directed to the incorporation of a prilocaine/lidocaine (50/50) eutectic into a PEO/hydroxypropylmethyl cellulose/polydextrose (70/10/20) film base at the 50 mg dose level in a 110 mg strip. Droplets of eutectic oil are captured in the film base during the drying of the film. The film base, when wetted, is useful as a dispersion of a prilocaine/lidocaine eutectic. The prilocaine/lidocaine eutectic is an oil at room temperature and therefore permits better skin penetration than the corresponding salt forms.

The components of the film are shown below in Table H:

TABLE H

| Components | Wt (g) |
|---|---|
| Polyethylene oxide WSR-N80 | 5.82 |
| Hydroxypropylmethyl cellulose E15 | 0.83 |
| Polydextrose | 1.66 |
| Lidocaine/Prilocaine (50/50) Eutectic Mixture | 7.95 |

TABLE H-continued

| Components | Wt (g) |
|---|---|
| Sodium chloride | 1.056 |
| Menthol | 0.17 |

In order to obtain the prilocaine base needed to form a eutectic with lidocaine, the HCl salt of prilocaine was neutralized with NaOH according to the following reaction, which was performed in situ, as described in further detail below:

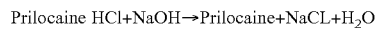

Prilocaine HCl+NaOH→Prilocaine+NaCL+H$_2$O

The procedure used to make the film product will now be described. Distilled water (29.29 g) was first added to a Degussa 1100 bowl. Then, 4.636 g of prilocaine HCl, 3.61 g of a 20% NaOH solution (containing 0.722 g NaOH and 2.88 g water) and 3.977 g of lidocaine were added to the bowl, in the order mentioned. Subsequently, 0.17 g of menthol and a blend of polyethylene oxide, hydroxypropylmethyl cellulose and polydextrose were added to the bowl. The combination of components was mixed using the Degussa Dental Multivac Compact under the conditions set forth in Table I below.

TABLE I

| Time (min) | Mixing Speed (rpm) | Vacuum (Hg) |
|---|---|---|
| 20 | 125 | 17 |
| 20 | 125 | 24 |
| 12 | 125 | 26.5 |
| 8 | 125 | 28 |

The resulting solution was cast into film using the K-Control Coater with the micrometer adjustable wedge bar set at 550 microns onto the HDP side of 6330. The film was dried 17 minutes in an 80° C. oven to about 2.83% moisture. The film was cut into 1¼×1 inch strips, which weighed 107 mg.

The resulting film was a dry film which contained a dispersion of the eutectic oil, as observed under the microscope. This observation was made when water was added to the film, as further described below.

The dry film had excellent tear resistance, was only slightly sticky and had adequate strength when pulled. It also had a film adhesion rating of 6 from the HDP side of 6330, and cut satisfactorily with die.

When skin was wetted, and the film was placed on the wetted skin, the film began to dissolve and turn opaque, indicating that the eutectic oil was being released as small emulsion-type droplets. The released oil was absorbed into the skin over time, as indicated by a decrease in the opaqueness of the film.

Example 6

Preparation of Nanometer Size Simvastatin Slurry

Ten grams of simvastatin (Biogal), having a particle size of from 10 to 100 microns is combined with 100 ml of distilled water and 2 grams of Cremophor RH 40. The combination is added to a micro lab sized micromill. The micromill is operated for about 1 hour, and the slurry is then examined under a microscope. The resulting particles are all smaller than 1 micron, indicating submicron nanometer-sized particles.

Example 7

Preparation of Film Using Nanometer Size Simvastatin Slurry

Forty two grams of nanometer sized simvastatin slurry are prepared using the method of Example 6. The resulting slurry contains 8.929% simvastatin. The slurry is added to a glass bowl and mixed with additives to create a polymeric matrix. The polymeric matrix includes the components set forth in Table J below.

TABLE J

| Components | Wt (g) |
| --- | --- |
| Simvastatin | 3.75 |
| Cremophor RH 40 | 0.75 |
| Water | 37.5 |
| HPMC | 3.437 |
| Polyethylene Oxide | 1.719 |
| Xylitol | 1.719 |
| Sucralose | 0.375 |
| Menthol flavor | 0.125 |

The combination is stirred for about 40 minutes at 125 rpm under a vacuum of 60% (16 in Hg); then stirred for another about 40 minutes at 125 rpm under a vacuum of 90% (25 in Hg); then stirred for about 20 minutes at 125 rpm under a vacuum of 95% (26 in Hg); and stirred for about 8 minutes at 125 rpm under a vacuum of 98% (27 in Hg). To the mixture is added 0.625 g peppermint flavor, and the resulting mixture is stirred for about 8 minutes at 100 rpm under a vacuum of 100% (28 in Hg). The solution is then cast into a film using a coating mechanism onto the HDP side of a polymeric or paper substrate. The film is dried for 25 minutes in an 80° C. convection air oven. The film is then cut into 0.875×1.25 inch strips which each weigh 66.67 mg. Film strips are then observed under a microscope, where no particles greater than 1 micron are observed. This indicates that all particles in the film are submicron in size, and there has been no agglomeration of particles.

Example 8

Preparation of Nanometer Size CoQ10 Emulsion

Ten grams of CoQ10 (Spectrum), having an average particle size of 20 to 150 microns is mixed with 3 grams of Cremophor EL (BASF) and 5 grams of Sesame oil. The mixture is heated to a temperature of 80° C. until the CoQ10 is dissolved in the Cremophor/Sesame oil mixture. The resulting mixture is added drop wise to 200 ml of distilled water, as it is pumped through a microfluidics high pressure pump. Pressure was set at 10,000 psi and 120 ml/min flow rate. The resulting emulsion is collected and cooled with an in-line cooler. The resulting emulsion is recycled three times through the apparatus. The resulting droplet is viewed through a microscope, and no droplets are seen to be larger than 1 micron. This indicates that the resulting droplets are submicron in size, and there has been no agglomeration of particles.

Example 9

Preparation of Film Using Nanometer Size CoQ10 Emulsion 90.83 grams of the nanometer size CoQ10 emulsion containing 4.587% CoQ10 are prepared as set forth in Example 8 above. The emulsion is used to prepare a wet matrix of 108.33 grams, including 25 grams of solids and 83.33 grams of water. The wet matrix contains the components set forth in Table K below.

TABLE K

| Components | Wt (g) |
| --- | --- |
| CoQ10 | 4.1665 |
| Cremophor EL | 1.250 |
| Sesame oil | 2.084 |
| Water | 83.33 |
| HPMC E15 | 7.625 |
| Polyethylene oxide | 3.813 |
| Xylitol | 3.813 |
| Sucralose | 0.75 |
| Menthol flavor | 0.25 |

The combination is stirred for about 40 minutes at 125 rpm under a vacuum of 60% (16 in Hg); then stirred for another about 40 minutes at 125 rpm under a vacuum of 90% (25 in Hg); then stirred for about 20 minutes at 125 rpm under a vacuum of 95% (26 in Hg); and stirred for about 8 minutes at 125 rpm under a vacuum of 98% (27 in Hg). To the mixture is added 1.250 g peppermint flavor, and the resulting mixture is stirred for about 8 minutes at 100 rpm under a vacuum of 100% (28 in Hg). The solution is then cast into a film using a coating mechanism onto the HDP side of a paper substrate. The film is dried for 25 minutes in an 80° C. convection air oven. The film is then cut into 0.875×1.25 inch strips which each weigh 66.67 mg. Film strips are then observed under a microscope, where no oil droplets greater than 1 micron are observed. This indicates that all droplets in the film are submicron in size, and there has been no agglomeration of droplets.

Example 10

Preparation of Nanometer Size Cyclosporine Slurry 0.5 grams of cyclosporine and 4.5 grams of Vitamin E (TPGS) were placed in a vial and heated in an 80° C. air oven until melted. The solution was taken out of the oven and allowed to cool. The sample was submitted for microscopy evaluation. It was determined that the cyclosporine was maintained in a small, nanoparticle size.

Example 11

Preparation of Film Incorporating Small-Scale Cyclosporine

The goal was to incorporate cyclosporine in an oral film strip at the 2 mg dosage level as a small-scale active (particularly in the size of a nanoparticle or in a nanosolution). The film composition included the components set forth in Table L below:

TABLE L

| Components | Wt (g) |
| --- | --- |
| Polyethylene Oxide (WSR N80) | 5.831 g |
| HPMC | 3.334 g |
| Cyclosporine slurry | 3.334 g |
| Simethicone | 0.001 g |
| Distilled water | 37.5 g |

The cyclosporine slurry was prepared as in Example 8 above, using 0.334 g of cyclosporine and 3.0 g of Vitamin E (TPGS). The cyclosporine slurry, simethicone, and distilled water were added to a fabricated glass bowl. The solution was prepared as described below.

First, the solution was mixed for 4 minutes while stirring at 150 rpm at 0% vacuum. The bowl was then equipped with a heating mantel and the heat was turned on. The solution was stirred for 12 minutes, stirring at 150 rpm at a temperature of 30° C. and 0% vacuum. The solution was then stirred for 8 minutes, stirring at 200 rpm, in a 0% vacuum at a temperature of 40° C. The heat was then turned off, and the blend of polyethylene oxide and HPMC were added to the bowl.

The solution was then stirred for 4 minutes at 125 rpm in a 60% vacuum (16 in Hg). Distilled water was then added to the mixture to reduce the solids to about 20%. The solution was then stirred for 4 minutes at 100 rpm in a vacuum of 60% (16 in Hg). One drop of simethicone and water were added to reduce the solids to about 18%. The solution was then stirred for 12 minutes at 100 rpm in a 60% vacuum (16 in Hg). The solution was then stirred for 20 minutes at 100 rpm in a 90% vacuum (25 in Hg), and then stirred for 8 minutes at 100 rpm in a 95% vacuum (26 in Hg). The solution was then stirred for 12 minutes at 100 rpm in a 98% vacuum (27 in Hg), and finally stirred for 8 minutes at 100 rpm in a 100% vacuum (28 in Hg).

The solution was then cast into films using a K-Control Coater with the micrometer adjustable wedge bar set at 770 microns. The film was dried for 28 minutes in an 80° C. air oven. The film was then cut into ⅜×1.25 inch strips. The moisture content of the strips was found to be 0.00%. Each strip weighed about 70 mg. The film strips had good tear resistance and had adequate strength when pulled. The strips were sealed in foil and submitted for evaluation.

What is claimed is:

1. A self-supporting film composition comprising:
   (i) a water soluble polymer composition comprising polyethylene oxide and a saccharide-based polymer; and
   (ii) a topical agent;
   wherein said topical agent is in the form of a small-scale particle selected from the group consisting of at least one type of nanoparticle, at least one type of micelle, at least one type of microdroplet, at least one type of microparticle, at least one type of liquid crystal, and combinations thereof, and
   wherein said small-scale particle of at least one agent is uniformly distributed in the film composition and uniformity is measured by equally sized individual unit doses which do not vary by more than 10% by weight of said small-scale particle of at least one agent from a desired dose.

2. The composition of claim 1, wherein said topical agent is in the form of at least one type of liquid crystal.

3. The composition of claim 1, wherein said topical agent is in the form of at least one type of micelle.

4. The composition of claim 1, wherein said topical agent is bound to at least one ligand.

5. A dosage composition comprising:
   a. A self-supporting film comprising:
      i. At least one polymer; and
      ii. At least one agent;
   wherein said at least one agent is in the form of a small-scale particle selected from the group consisting of at least one type of nanoparticle, at least one type of micelle, at least one type of microdroplet, at least one type of microparticle, at least one type of liquid crystal, and combinations thereof, and
   wherein said small-scale particle of at least one agent is uniformly distributed in the dosage composition and uniformity is measured by equally sized individual unit doses which do not vary by more than 10% by weight of said small-scale particle of at least one agent from a desired dose.

6. The composition of claim 5, wherein said agent is in the form of at least one type of liquid crystal.

7. The composition of claim 5, wherein said agent is in the form of at least one type of micelle.

8. The composition of claim 5, wherein said agent is bound to at least one ligand.

9. A method of forming a self-supporting film dosage composition, comprising the steps of:
   a. Providing a polymeric matrix;
   b. Forming a small-scale form of at least one agent;
   c. Dispersing said small-scale form of at least one agent throughout said polymeric matrix;
   d. Drying said polymeric matrix so as to form a self-supporting film dosage composition comprising said small-scale form of at least one agent;
   wherein said small-scale form of at least one agent is selected from the group consisting of at least one type of nanoparticle, at least one type of microparticle, at least one type of microdroplet, at least one type of micelle, at least one type of liquid crystal, and combinations thereof, and
   wherein said small-scale form of at least one agent is uniformly distributed in the film dosage composition and uniformity subsequent to dispersing and drying is measured by equally sized individual unit doses which do not vary by more than 10% by weight of said small-scale form of at least one agent from a desired dose.

10. The method of claim 9, wherein said agent is in the form of at least one type of microdroplet.

11. The method of claim 9, wherein said agent is in the form of at least one type of micelle.

12. The method of claim 9, wherein said small-scale form of at least one agent is formed through emulsion processing.

13. The method of claim 9, wherein said small-scale form of at least one agent is formed through milling.

14. The method of claim 9, wherein said small-scale form of at least one agent is formed through processing via a microfluidics pumping apparatus.

15. The method of claim 9, wherein said small-scale form of at least one agent is bound to at least one ligand.

16. The method of claim 9, wherein said step of drying said polymeric matrix comprises heating said polymeric matrix so as to rapidly form a visco-elastic mass to maintain a uniform distribution of said agent by locking-in or preventing migration of said agent within said visco-elastic mass within the first 10 minutes or less to maintain a uniform distribution of said agent by locking-in or preventing migration of said agent within said visco-elastic mass.

17. The method of claim 16, wherein said polymeric matrix containing said agent varies no more than 10% by weight of said agent throughout said polymeric matrix.

18. The method of claim 16, wherein said step of drying said polymeric matrix further comprises further drying said visco-elastic mass so as to provide a self-supporting film dosage composition having a solvent content of 10% or less.

19. The method of claim 16, wherein said step of forming a visco-elastic mass occurs within the first 0.5 to about 10 minutes of heating to maintain a uniform distribution of said agent by locking-in or preventing migration of said agent within said visco-elastic mass.

20. The method of claim 19, wherein said polymeric matrix containing said agent varies no more than 10% by weight of said agent throughout said polymeric matrix.

21. The method of claim 19, wherein said step of drying said polymeric matrix further comprises further drying said visco-elastic mass so as to provide a self-supporting film dosage composition having a solvent content of 10% or less.

22. The method of claim 9, wherein said small-scale form of at least one agent is formed through processing via a high shear apparatus.

23. The method of claim 9, wherein said small-scale form of said agent is in the form of at least one liquid crystal.

24. A method of forming a self-supporting film dosage composition, comprising the steps of:
   a. Providing a polymeric matrix;
   b. Forming a small-scale form of at least one agent;
   c. Applying said small-scale form of at least one agent to said polymeric matrix via deposition; and
   d. Drying said polymeric matrix so as to form a self-supporting film dosage composition comprising said small-scale form of at least one agent,
   wherein said small-scale form of at least one agent is selected from the group consisting of at least one type of nanoparticle, at least one type of micelle, at least one type of microdroplet, at least one type of microparticle, at least one type of liquid crystal, and combinations thereof, and
   wherein said small-scale form of at least one agent is uniformly distributed on the film dosage composition and uniformity subsequent to applying and drying is measured by equally sized individual unit doses which do not vary by more than 10% by weight of said small-scale form of at least one agent from a desired dose.

25. The method of claim 24, wherein said agent is in the form of at least one type of microdroplet.

26. The method of claim 24, wherein said agent is in the form of at least one type of micelle.

27. The method of claim 24, wherein said small-scale form of at least one agent is formed through emulsion processing.

28. The method of claim 24, wherein said small-scale form of at least one agent is formed through milling.

29. The method of claim 24, wherein said small-scale form of at least one agent is formed through processing via a microfluidics pumping apparatus.

30. The method of claim 24, wherein said small-scale form of at least one agent is bound to at least one ligand.

31. The method of claim 24, wherein said small-scale form of at least one agent is formed through processing via a high shear apparatus.

32. The method of claim 24, wherein said small-scale form of said agent is in the form of at least one liquid crystal.

* * * * *